(12) United States Patent
Kompella et al.

(10) Patent No.: US 7,939,541 B2
(45) Date of Patent: May 10, 2011

(54) INTERMEDIATES AND A PROCESS EMPLOYING THE INTERMEDIATES FOR THE PREPARATION OF (3-TRIFLUOROMETHYLSULFONYL)-N-[4-METHYL-3-(4-PYRIDIN-3YL-PYRIMIDIN-2YLAMINO)-PHENYL]-BENZAMIDE

(75) Inventors: Amala kishan Kompella, Hyderabad (IN); Bhujanga rao Adibhatla Kali Satya, Hyderabad (IN); Sreenivas Rachakonda, Hyderabad (IN); Nannapaneni Venkaiah Chowdary, Hyderabad (IN)

(73) Assignee: Natco Pharma Limited, Hyderabad (IN)

( * ) Notice: Subject to any disclaimer, the term of this patent is extended or adjusted under 35 U.S.C. 154(b) by 295 days.

(21) Appl. No.: 12/042,240

(22) Filed: Mar. 4, 2008

(65) Prior Publication Data

US 2008/0249121 A1 Oct. 9, 2008

Related U.S. Application Data

(63) Continuation-in-part of application No. 11/714,565, filed on Mar. 5, 2007, which is a continuation-in-part of application No. PCT/IN2005/00243, filed on Jul. 19, 2005.

(30) Foreign Application Priority Data

Sep. 9, 2004 (IN) ............................ 908/CHE/2004

(51) Int. Cl.
*C07D 401/04* (2006.01)
*A61K 31/506* (2006.01)
(52) U.S. Cl. ......... 514/275; 544/331; 564/164; 564/166
(58) Field of Classification Search ................... 544/331; 514/275; 564/164, 166
See application file for complete search history.

(56) References Cited

FOREIGN PATENT DOCUMENTS

| EP | 0 564 409 | 10/1993 |
|---|---|---|
| WO | WO 95/09847 | 4/1995 |
| WO | WO 99/15164 A | 4/1999 |
| WO | WO 02/22597 | 3/2002 |
| WO | WO 2004/029038 A | 4/2004 |
| WO | WO 2004/110452 A | 12/2004 |
| WO | WO 2006/027795 A1 | 3/2006 |

OTHER PUBLICATIONS

Simone, Oncology: Introduction, Cecil Textbook of Medicine, 20$^{th}$ Edition, vol. 1, pp. 1004-1010, 1996.*
Gura, Systems for identifying New Drugs Are Often Faulty, Cancer Models, Science, vol. 278, No. 5340, pp. 1041-1042, Nov. 2007.*
Johnson et al., Relationships between drug activity in NCI preclinical in vitro and in vivo models and early clinical trials, British Journal of Cancer (2001) 64(10): 1424-1431.*
Invitation to Pay Additional Fees with Partial International Search mailed Jul. 15, 2009.
Ogata et al. "Synthesis and Antiviral activity of sulphonamidobenzophenone oximes and sulphonamidobenzamides." *Journal of Medicinal Chemistry.* vol. 29, No. 3. 1986. pp. 417-423.
Zimmermann et al. "Potent and selective inhibitors of the Abl-kinase: Phenylaminopyrimidine (PAP) derivatives." *Bioorganic and Medicinal Chemistry Letters.* vol. 7, No. 2. 1997. pp. 187-192.
Schindler et al. "Structural mechanism for STI-571 inhibition of Abelson tyrosine kinase." *Science.* vol. 289, No. 5486. 2000. pp. 1938-1942.
Examination Report from corresponding European Application No. 05 779 775.5-2101 dated Feb. 16, 2010.
Examination Report from corresponding European Application No. 05 779 775.5-2101 dated Apr. 25, 2008.

* cited by examiner

*Primary Examiner* — Deepak Rao
(74) *Attorney, Agent, or Firm* — Merchant & Gould P.C.

(57) ABSTRACT

This invention relates to a process for the preparation of (3-trifluoromethylsulfonyl)-N-[4-methyl-3-(4-pyridin-3yl-pyrimidin-2ylamino)-phenyl]-benzamide (formula (I)) starting from 4-methyl-2-nitro-aniline (formula (II)) through intermediates (3-trifluoromethylsulfonyl)-N-[4-methyl-3-nitrophenyl]-benzamide (formula (III)), (3-trifluoromethylsulfonyl)-N-[3-amino-4-methylphenyl]-benzamide (formula (IV)) and (3-trifluoromethylsulfonyl)-N-[3-guanidino-4-methylphenyl]-benzamide (formula (V)). This invention also relates to processes for the preparation of these intermediates. The compound of formula (I), also known as AN-024, is:

Formula I

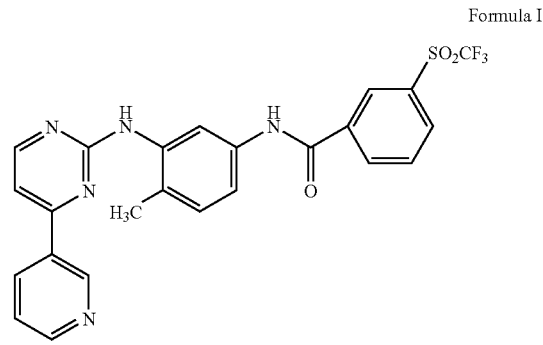

Development code: AN-024

9 Claims, 16 Drawing Sheets
(13 of 16 Drawing Sheet(s) Filed in Color)

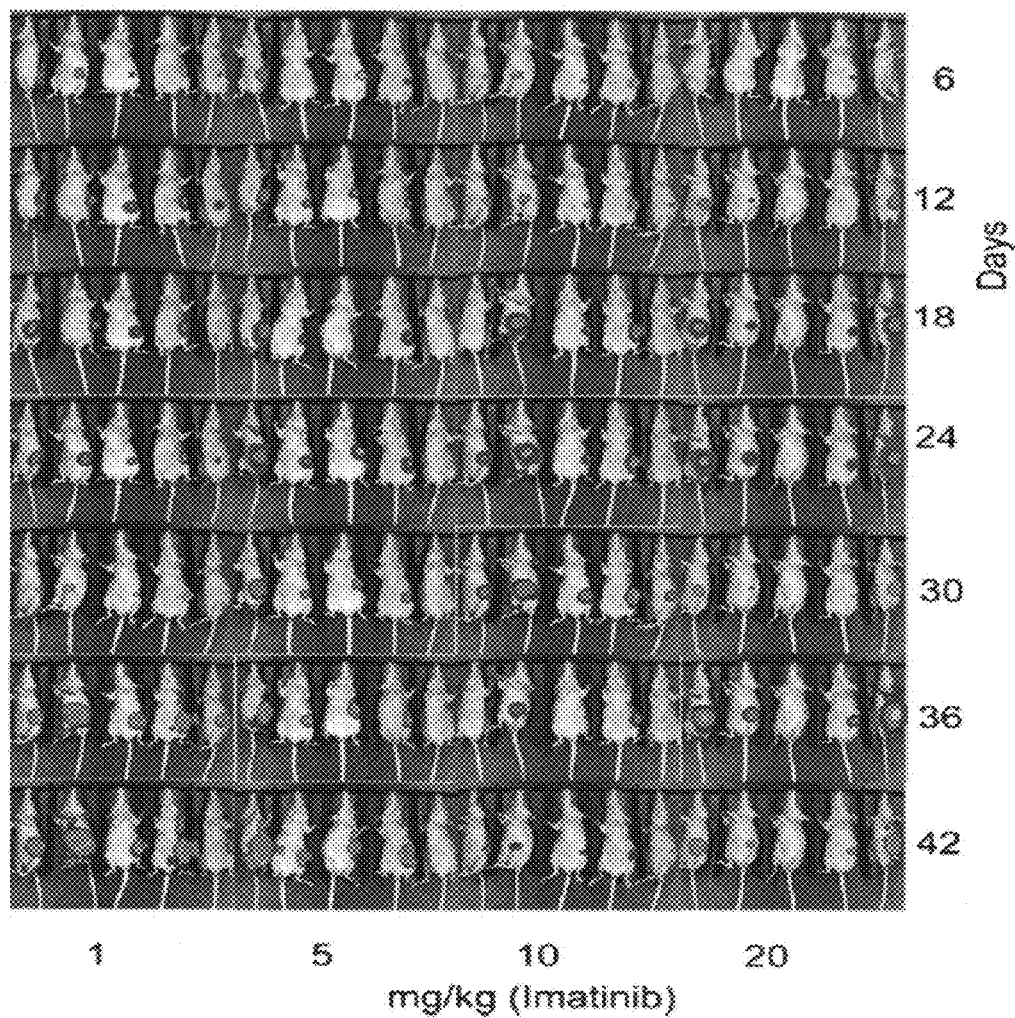
Figure 8. The figure shows luciferase expression intensity of K562 luc cells implanted in nude mice followed by oral treatment of Imatinib.

INTERMEDIATES AND A PROCESS EMPLOYING THE INTERMEDIATES FOR THE PREPARATION OF (3-TRIFLUOROMETHYLSULFONYL)-N-[4-METHYL-3-(4-PYRIDIN-3YL-PYRIMIDIN-2YLAMINO)-PHENYL]-BENZAMIDE

This application is a Continuation-in-Part of application Ser. No. 11/714,565, filed 5 Mar. 2007, which is the Continuation-in-Part of International Application No. PCT/IN2005/00243, filed 19 Jul. 2005, and which application(s) are incorporated herein by reference.

FIELD OF THE INVENTION

This invention relates to a process for the preparation of (3-trifluoromethylsulfonyl)-N-[4-methyl-3-(4-pyridin-3yl-pyrimidin-2ylamino)-phenyl]-benzamide (formula (I)) starting from 4-methyl-2-nitro-aniline (formula (II)) through intermediates (3-trifluoromethylsulfonyl)-N-[4-methyl-3-nitrophenyl]-benzamide (formula (III)), (3-trifluoromethylsulfonyl)-N-[3-amino-4-methylphenyl]-benzamide (formula (IV)) and (3-trifluoromethylsulfonyl)-N-[3-guanidino-4-methylphenyl]-benzamide (formula (V)). This invention also relates to processes for the preparation of these intermediates. The compound of formula (I), also known as AN-024, is:

Formula-1

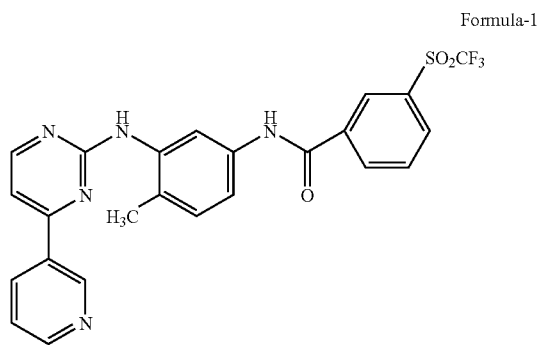

Development code: AN-024

BACKGROUND OF THE INVENTION

The preparation of (3-trifluoromethylsulfonyl)-N-[4-methyl-3-(4-pyridin-3yl-pyrimidin-2ylamino)-phenyl]-benzamide of formula (I), and the use thereof, especially as an anti-tumor agent, are described in Example 13 of US 2007/0232633, which was published on Oct. 4, 2007, and in corresponding applications in numerous other countries (PCT/IN 2005/000243).

In view of usefulness of (3-trifluoromethylsulfonyl)-N-[4-methyl-3-(4-pyridin-3yl-pyrimidin-2ylamino)-phenyl]-benzamide (formula (I)) for society and the health-care industry as an anti tumor agent, a process for the preparation of the compound of formula (I) was developed.

SUMMARY OF THE INVENTION

The present invention relates to the preparation of intermediates and a process for the preparation of 3-trifluoromethylsulfonyl)-N-[4-methyl-3-(4-pyridin-3yl-pyrimidin-2ylamino)-phenyl]-benzamide of formula (I) employing the intermediates. (3-Trifluoromethylsulfonyl)-N-[4-methyl-3-(4-pyridin-3yl-pyrimidin-2ylamino)-phenyl]-benzamide of formula (I), is an antiproliferative (e.g., anti-tumor) agent.

Accordingly the present invention provides a process for the preparation of the compound of formula (I) which includes (as shown in Scheme I below):
(a) Providing (3-trifluomethylsulfonyl)benzoyl chloride (formula (VI)) or preparing it by conventional methods;
(b) Condensing 4-methyl-2-nitro-aniline (formula (II)) with a compound of formula (XI) at about 30 to about 40° C. in chlorohydrocarbon solvent with aqueous alkali addition to obtain (3-trifluoromethylsulfonyl)-N-[4-methyl-3-nitrophenyl]-benzamide (formula (III))
(c) Reducing the compound of formula (III) with stannous chloride/conc. HCl at about 0 to about 5° C. for about 3 to about 4 hours to obtain (3-trifluoromethylsulfonyl)-N-[3-amino-4-methylphenyl]-benzamide (formula (IV));
(d) Condensing the compound of formula (IV) with cyanamide solution at about 90 to about 95° C. in n-butanol solvent to obtain (3-trifluoromethylsulfonyl)-N-[3-guanidino-4-methylphenyl]-benzamide (formula (V));
(e) Condensing the compound of formula (V) with a compound of formula (VII) in presence of base at reflux temperature to obtain the compound of formula (I).

In an embodiment, the present invention provides a process for the preparation of a compound of formula (III) which includes:
(a) Providing (3-trifluomethylsulfonyl) benzoyl chloride (formula (VI)); or preparing it by conventional methods;
(b) Condensing 4-methyl-2-nitro-aniline (formula (II)) with the compound of formula (VI) at about 30 to about 40° C. in chlorohydrocarbon solvent with aqueous alkali addition to obtain (3-trifluoromethylsulfonyl)-N-[4-methyl-3-nitrophenyl]-benzamide (formula (III)).

In an embodiment, the present invention provides a process for the preparation of (3-trifluoromethylsulfonyl)-N-[3-amino-4-methylphenyl]-benzamide (formula (IV)) which includes:
a) Providing (3-trifluomethylsulfonyl)benzoyl chloride (formula (VI)); or preparing it by conventional methods;
b) Condensing 4-methyl-2-nitro-aniline (formula (II)) with the compound of formula (VI) at about 30 to about 40° C. in chlorohydrocarbon solvent with aqueous alkali addition to obtain (3-trifluoromethylsulfonyl)-N-[4-methyl-3-nitrophenyl]-benzamide (formula (III));
c) Reducing the compound of formula (III) with stannous chloride/conc. HCl at about 0 to about 5° C. for about 3 to about 4 hours to obtain (3-trifluoromethylsulfonyl)-N-[3-amino-4-methylphenyl]-benzamide (formula (IV)).

In an embodiment, the present invention provides a process for the preparation of N-{2-(4-methylpiperazinomethyl)benzoylamido]-5-methyl}guanidine hydrochloride (formula (V)) which includes:
(a) Providing (3-trifluomethylsulfonyl) benzoyl chloride (formula (VI)); or preparing it by conventional methods;
(b) Condensing 4-methyl-2-nitro-aniline (formula (II)) with the compound of formula (VI) at about 30 to about 40° C. in chlorohydrocarbon solvent with aqueous alkali addition to obtain (3-trifluoromethylsulfonyl)-N-[4-methyl-3-nitrophenyl]-benzamide (formula (III));
(c) Reducing the compound of formula (III) with stannous chloride/conc. HCl at about 0 to about 5° C. for about 3 to about 4 hours to obtain (3-trifluoromethylsulfonyl)-N-[3-amino-4-methylphenyl]-benzamide (formula (IV));
(d) Condensing the compound of formula (IV) with aqueous cyanamide at about 90 to about 95° C. in n-butanol solvent to obtain (3-trifluoromethylsulfonyl)-N-[3-guanidino-4-methylphenyl]-benzamide (formula (V)).

BRIEF DESCRIPTION OF THE FIGURES

The patent application file contains at least one drawing executed in color. Copies of this patent or patent application publication with color drawing(s) will be provided by the Office upon request of payment of the necessary fee.

FIGS. 3A and 3B. Decreased luciferase expression in nude mice implanted with K562 luc human leukemia cells and treated with AN024 or Imatinib (Example 4). AN024 at a concentration of 1 mg/kg did not induce a decrease in luciferase expression, whereas 5 mg/kg, 10 mg/kg, and 20 mg/kg concentrations caused a decrease in luciferase expression. Imatinib administration at 1 mg/kg concentration did not induce a decrease in luciferase expression, whereas 10 mg/kg and 20 mg/kg did show a retardation of luciferase expression.

FIG. 4A (Example 6) is a graphical representation of the decrease in the blast cell count by the oral (or) administration of Dasatinib in nude mice implanted with Baf3 mutant cells (wt, T315I, M351T and E255K). FIG. 4B (Example 6) is a graphical representation of the decrease in the blast cell count by the oral (or) administration of Imatinib in nude mice implanted with Baf3 mutant cells (wt, T315I, M351T and E255K). FIG. 4C (Example 6) is a graphical representation of the decrease in the blast cell count by the oral (or) administration of AN-024 in nude mice implanted with Baf3 mutant cells (wt, T315I, M351T and E255K).

DETAILED DESCRIPTION OF THE INVENTION

The reaction scheme for the preparation of the compound of formula (I) according to the present invention is shown in scheme-1.

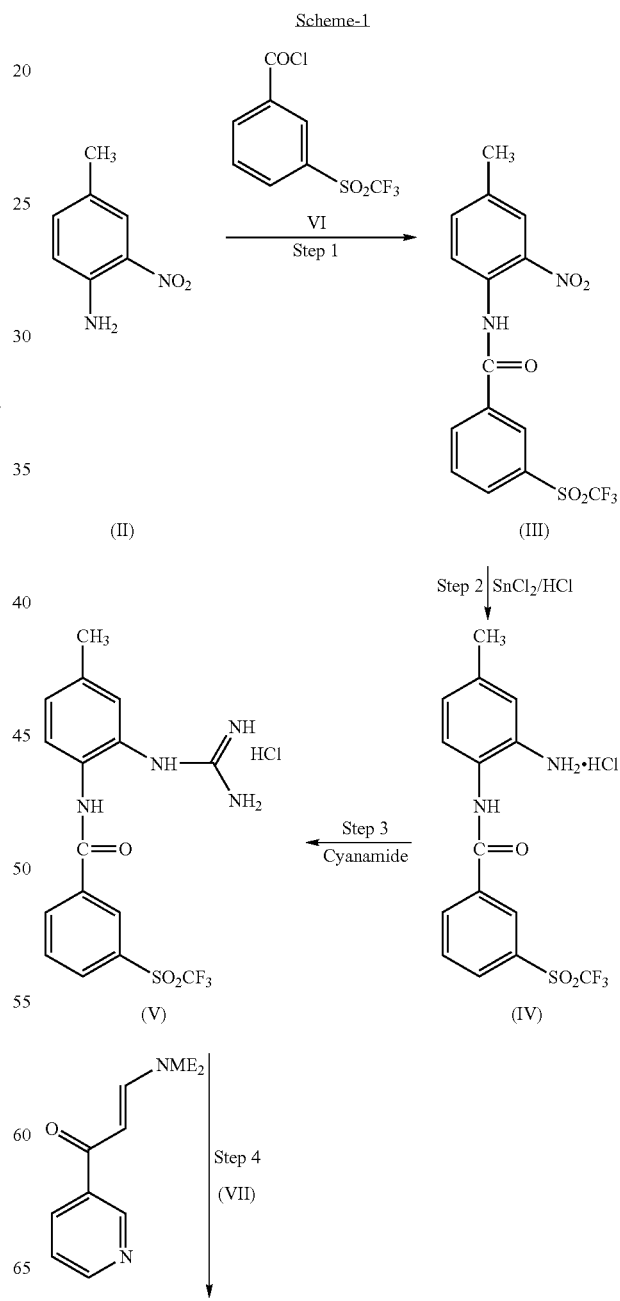

-continued

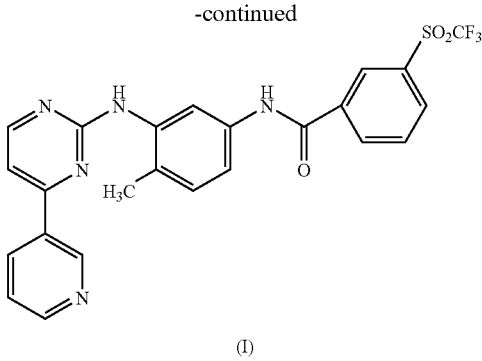

(I)

In an embodiment of the reaction of Scheme 1, in step 1, the alkali can be sodium hydroxide or potassium hydroxide, for example, potassium hydroxide. This reaction can be conducted in a chlorinated hydrocarbon such as methylene chloride or chloroform, for example, chloroform. The temperature can be in the range about 30 to about 40° C.

In an embodiment, the reduction in step 2 can be effected by employing 6 moles of stannous chloride in conc. HCl medium. In an embodiment, the solvent used in step 3 can be n-butanol. In an embodiment, step 4 of the present invention can be carried out employing sodium hydroxide in the presence of n-butanol.

The disclosures of U.S. patent application Ser. No. 11/714,565, filed Mar. 5, 2007 (U.S. Publication No. US 2007/0232633, published on Oct. 4, 2007) and of PCT Application No. PCT/IN 2005/000243, filed Jul. 19, 2005 (PCT Publication No. WO2006/027795, published on Mar. 16, 2006) are incorporated by reference herein in their entirety.

Embodiments of the present invention are described in the examples given below, which are provided to illustrate the invention only and therefore they should not be construed to limit the scope of the invention.

EXAMPLES

A compound of this invention of formula I (indicated by development code (AN-024)) was found to exhibit effective anti-proliferative (e.g., anti-tumor) activity. This anti-proliferative activity is superior to some of the existing approved drugs of this class. The development code AN-019 refers to another compound of the same class described elsewhere by the inventors. The bio-efficacy and activity of the compounds of this invention have been compared with the approved drugs like Imatinib mesylate and Dasatinib to serve as positive controls in this study. 'Imatinib mesylate' has been abbreviated as referred to as 'Imatinib' in this study.

Example 1

Figure 1:
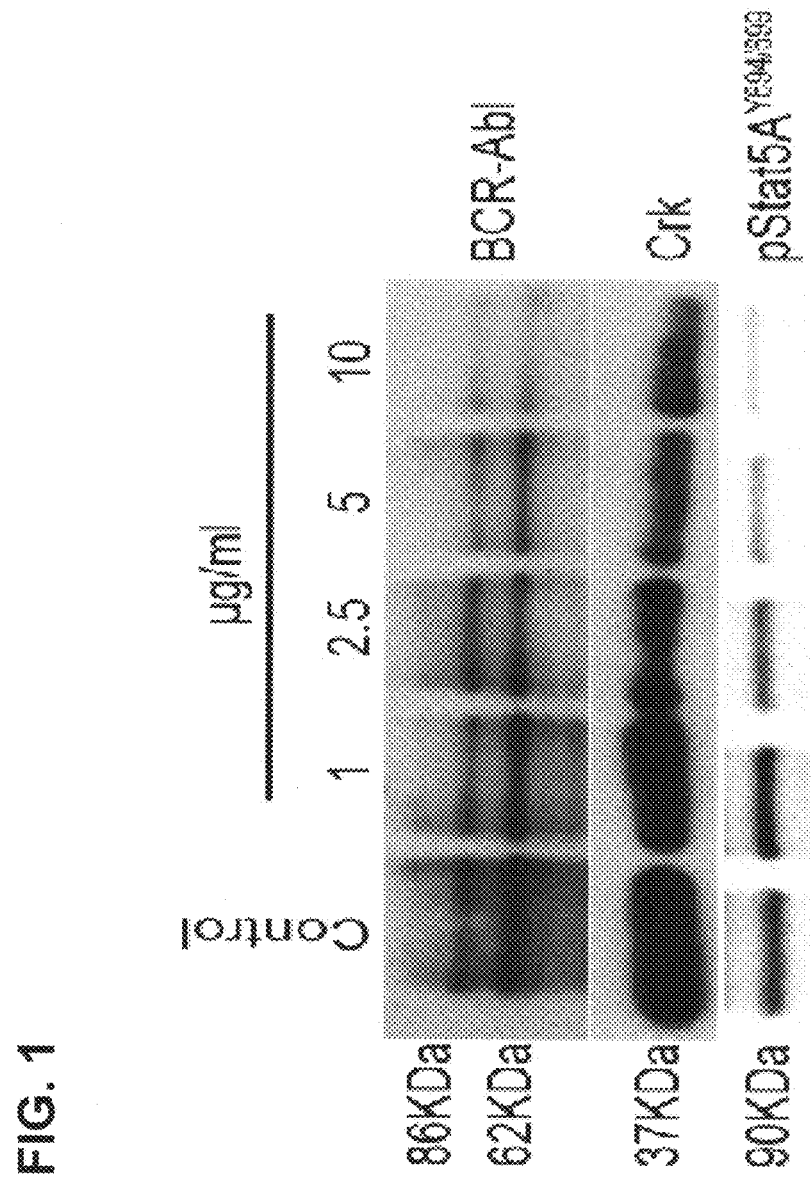
FIG. 1. K562 cells were treated with various concentrations of AN024 (1-10 μg/ml). Cell lysates were collected and western blot analysis was performed per standard protocols. Expression levels of BCR-Abl, Crk and Stat5AY$^{694/699}$ were determined (Example 1).

Establishment of Anti-CML Activity of AN-024 in Nude Mice Implanted With k562 Cells (FIG. 1)

In Vitro Studies with AN-024

Expression levels of BCR-Abl, Crk and phospho Stat5AY$^{694/699}$ were determined by western blot analysis in K562 cells treated with various concentrations of AN024 (1, 2.5, 5 or 10 µg/ml) for 12 h. It was observed that BCR-Abl, Crk and phospho Stat5AY$^{694/699}$ protein levels decreased in a dose dependent manner.

Western Blot Analysis

K562 cells were treated with 1, 2.5, 5, or 10 µg/ml of AN024. After 12 h, cells were collected and total cell lysates were prepared in extraction buffer containing Tris [0.1 M, pH 7.5], Triton-X114 (1.0%), EDTA (10 mM), aprotinin, and phenylmethylsulphonyl fluoride. 10 µg of protein from these samples were separated under non-reducing conditions by 12% SDS-PAGE and transferred to nitrocellulose membranes (Schleicher & Schuell, Keene, N.H.). The membranes were probed for 2 h with antibodies against BCR-Abl, Crk and phospho Stat5AY$^{694/699}$ per standard protocols. The membranes were subsequently washed three times with PBS to remove excess primary antibodies, incubated with appropriate HRP conjugated secondary antibodies as required, and then developed according to enhanced chemiluminesence protocol (Amersham, Arlington Heights, Ill.).

MTT Cell Growth Assay

K562 cells were treated with various concentrations of AN024 (1, 2.5, 5, or 10 µg/ml) for 24 h, following which MTT assay was performed to determine the proliferative index of the treated cells. The assay was performed per standard protocols according to manufacturer's instructions (Chemicon Temecula, Calif.). Optical density was measured at 570 nm and graphically represented. Absorbance was directly proportional to the number of cells present and the number of viable cells determined.

AN024 inhibited BCR-Abl kinase activity in a dose dependent manner.

FIG. 1 illustrates results of this testing. K562 cells were treated with various concentrations of AN024 (1-10 µg/ml). Cell lysates were collected and western blot analysis was performed per standard protocols. Expression levels of BCR-Abl, Crk and Stat5AY$^{694/699}$ were determined.

Example 2

Figure 2:
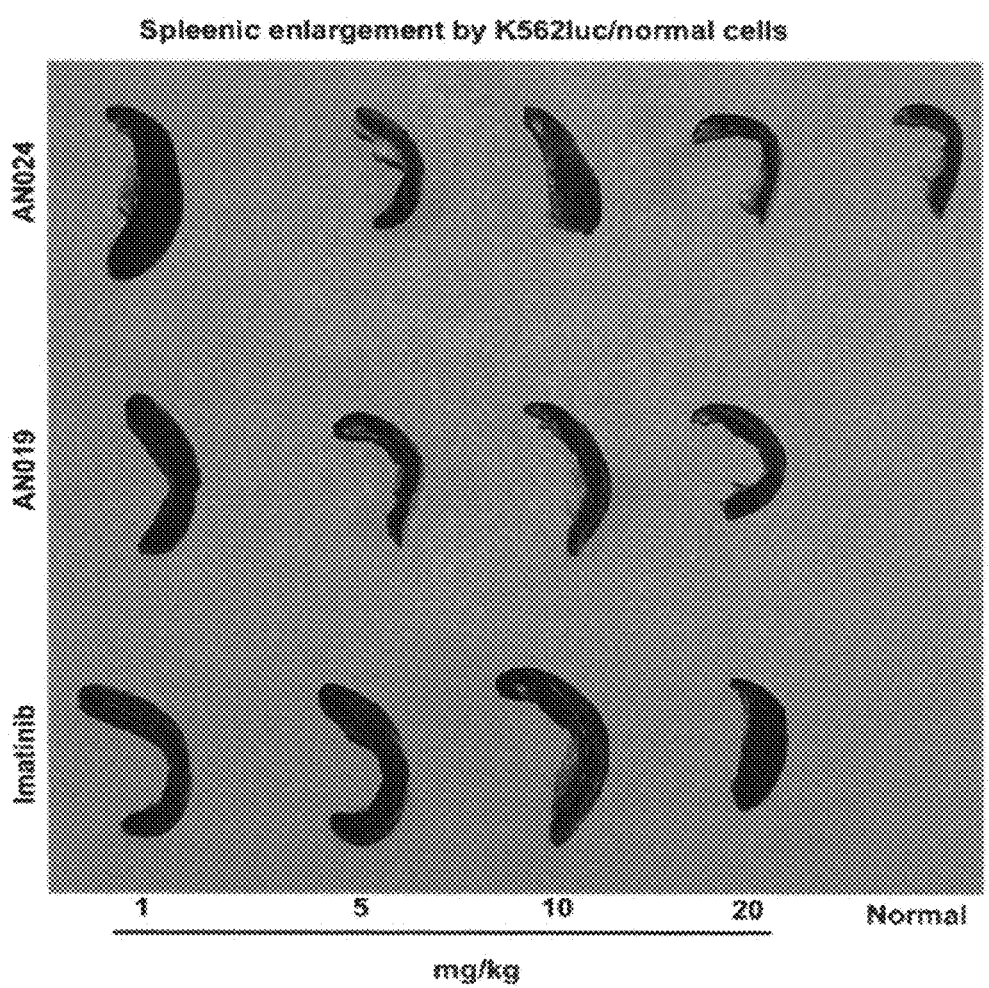
FIG. 2. Reduction in spleenic enlargement in K562 implanted nude mice by oral dosage of AN-024 and Imatinib (Example 2). Spleenic enlargement was determined by visual inspection and it was determined that control mice showed enlarged spleen indicative of K562 cellular localization. AN024-treated cells did not show any spleenic enlargement whereas Imatinib-treated mice showed slight spleenic enlargement.

AN024 Injections of Nude Mice Implanted with K562 Cells Did Not Show Spleenic Enlargement and No Crk Expression (FIG. 2)

Nude mice implanted with K562 cells were treated with Imatinib or AN024 via ip injections. Mice were sacrificed after a decrease in percent leukemia growth index (LGI) was observed and spleen harvested. Spleenic enlargement was determined by visual inspection and it was determined that control mice showed enlarged spleen indicative of K562 cellular localization. AN024-treated cells did not show any spleenic enlargement whereas Imatinib-treated mice showed slight spleenic enlargement. These results are shown in FIG. 2.

Paraffin sections of spleen immuno-probed for the presence of Crk protein showed strong localization of Crk expression accompanied with increased cellular density indicative of K562 localization in control mice. Mice treated with AN-024 showed only basal level expression of Crk expression comparable to negative control. Mice treated with Imatinib indicated localized expression regions of Crk expression, indicative of K562 cells in the spleen. Control mice also developed random subcutaneous tumors showing Crk expression, indicative of the presence of K562 cells.

From these results it is evident that AN024 treatment caused the regression of LGI in nude mice. Imatinib-treated mice also showed significant reduction in LGI but lagged AN-024 treated mice. Both AN024- and Imatinib-treated mice showed no abnormal physiological, phenotypic or behavioral abnormality. Control mice showed the presence of random subcutaneous tumors with loss of digits accompanied with reddish spots under the skin and a slight enlargement of the abdomen. From these results, it is evident that AN-024 has promise as a therapeutic drug for the treatment of leukemia.

Example 3

In Vivo Studies Using Baf3 Imatinib Resistant Murine CML Cell Lines

To determine the in vivo anti-leukemic activity of AN019 and AN024, nude mice were implanted intraperitoneally with Baf3 murine leukemia cells (Wt, T315I, M351T and E225K), and 15 days after implantation the mice were treated with Imatinib (10 mg/kg), AN019 (20mg/kg) and AN024 (20mg/kg) by oral gavage or ip injections. Blood smears were obtained via the tail vein or via the femoral vein every 6th day and blast cells counted and graphically represented.

Blood smears of Baf3Wt implanted mice treated with Imatinib (10 mg/kg), AN019 (20 mg/kg) or AN024 (20mg/kg) were similar to normal controls after 42 days.

Blood smears of Baf3T315I implanted mice treated with Imatinib (10 mg/kg), AN019 (20 mg/kg) or AN024 (20 mg/kg) showed a significant decrease in blast cell count in AN024 and AN019 treated mice. Mice treated with oral dosage of Imatinib did not show a decrease in blast cell count and were similar to untreated controls and Baf3M351T implanted mice.

Mice implanted with Baf3E255K also behaved similarly to Baf3M351T and Baf3T315I implanted mice.

Nude mice were implanted with Baf3 mutant cells Wt, E255K, T315I, and M351T were treated with Imatinib, AN019 and AN024 (orally and ip). Briefly, mice were treated with Imatinib (10 mg/kg), AN019 (20 mg/kg) and AN024 (20 mg/kg) by oral gavage or ip injections 15 days post-implantation. Abdominal swelling and decrease in activity was monitored daily, blood smear taken via the tail vein or the femoral vein every $6^{th}$ day and H&E stained as per standard protocols. 42 days after implantation, mice were sacrificed and spleens harvested. Spleenic enlargement was determined and correlated with blood smear blast cell count.

Results

Microscopic Determination of Blast Cell Count

Blood from tail vein or the femoral vein was taken every 6th day from Baf3 cell implanted mice until day 42. On the 15th day post-implantation, the mice were given treatments with Imatinib, AN019 and AN024 (orally and ip) as described earlier. It was observed that in Baf3Wt implanted mice, progressive decrease in blast cell count was observed in all treatment conditions. Baf3M351T, T315I and E225K did not respond well to Imatinib treatments. Oral administration of Imatinib had no significant effect in Baf3M351T, T315I and E225K implanted mice. Overall intraperitoneal treatments AN024 and AN019 were significantly better at decreasing blast cell count in all Baf3 implanted mice.

AN019 treatment in Baf3Wt implanted mice induced a complete regression of leukemic blast cells and was comparable to untreated controls. Intraperitoneal treatments were superior to oral treatments. AN019 treatment in Baf3 M351T, T315I and E225K implanted mice showed a significant decrease in blast cell count and was comparable to 12th day post-implant in ip-treated mice at day 42; ip-treated mice showed greater regression of blast cells than oral treated mice. AN024 treatment in Baf3 M351T, T315I and E225K implanted mice showed a significant decrease in blast cell count and was superior to AN019 treatment at day 42; ip-treated mice showed greater regression of blast cells than orally treated mice.

Example 4

Response of Nude Mice Implanted With K562 Normal/Luc Human Leukemic Cells With Low Dose of AN024, AN019 and Imatinib (FIGS. 3A and 3B) Oral Administration of AN019, AN024 and Imatinib

| | K562 luc | | | K562 normal | | |
|---|---|---|---|---|---|---|
| mg/kg | AN024 | AN019 | Imatinib | AN024 | AN019 | Imatinib |
| 1 | 5 | 5 | 5 | 5 | 5 | 5 |
| 5 | 5 | 5 | 5 | 5 | 5 | 5 |
| 10 | 5 | 5 | 5 | 5 | 5 | 5 |
| 20 | 5 | 5 | 5 | 5 | 5 | 5 |

Total = 120 animals

Nude mice (nu/nu) were implanted with K562 cells (1×106) normal/luc via tail vein. Five mice were used per group and divided into 24 groups+2 control. All groups were implanted with K562 normal/luc cells. Of the 24 groups, 12 were used for luciferase studies whereas the other 12 were used for blood smear count studies.

Drugs were administered by oral gavage as previously suggested (2% gum acacia and 2% SLS in an aqueous suspension).

Results

Oral administration of AN024 (1, 5, 10 and 20 mg/kg) in nude mice implanted with K562 luc human leukemia cells resulted in leukemia regression at higher concentrations. AN024 concentration at 1 mg/kg did not induce a decrease in luciferase expression, whereas 5 mg/kg, 10 mg/kg, and 20 mg/kg concentrations caused a decrease in luciferase expression.

Figure 3A:
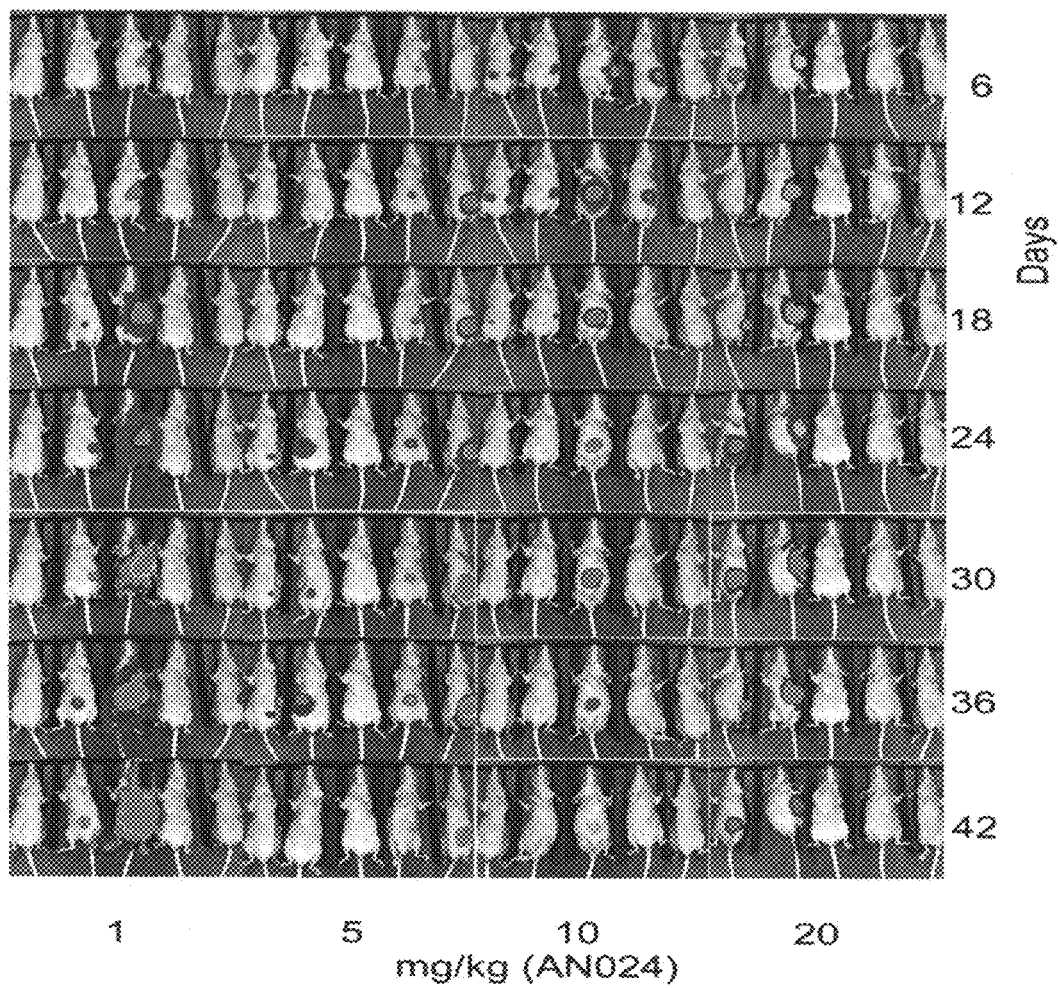

Oral administration of Imatinib (1, 5, 10 and 20 mg/kg) in nude mice implanted with K562 luc human leukemia cells resulted in leukemia regression at higher concentrations. Imatinib administration at 1 mg/kg concentration did not induce a decrease in luciferase expression, whereas 10 mg/kg and 20 mg/kg did show a retardation of luciferase expression. Leukemia regression was very pronounced in the animals treated with AN-024 and better than Imatinib. These results are illustrated in FIGS. 3A and 3B.

Example 5

Determination of Drug Effectiveness ($D_e$) and Drug Temporal Penetration Determination of Drug Effectiveness ($D_e$)

Drug effectiveness was determined using the equation, $$D_e = \left[ \sum \frac{alive}{luc} - \sum_C \frac{alive}{luc} \right] \div \sum_{C-initial} alive \times 100$$

Where:
$\Sigma alive$=total number of mice alive per concentration at the end of experiment times photon count, $\Sigma luc$=total number of mice alive showing luciferase expression per concentration at end of experiment and c represents control untreated animals times photon count and $\Sigma_{c\text{-}initial}$ represents the initial number of animals in control at start of experiment times photon count. The results were represented graphically as percent drug effectiveness (Table 1).

Results

Table 1 shows the drug effectiveness at various concentrations of Imatinib, AN019 and AN024 as determined from the in vivo studies. From Table 1 it is evident that AN019 behaved in a dose dependent manner, whereas Imatinib and AN024 do not, and were effective at low concentrations.

TABLE 1

| Drug | 5 mg/kg | 10 mg/kg | 20 mg/kg | 40 mg/kg |
|---|---|---|---|---|
| Imatinib $D_e$ | 10.00 | 32.00 | 13.33 | 8.00 |
| AN019 $D_e$ | 25.82 | 78.20 | 83.40 | 85.20 |
| AN024 $D_e$ | 30.00 | 85.00 | 87.00 | 90.00 |

Determination of Drug Temporal Penetrance ($T_p$)

The temporal penetrance was calculated applying the following equation, $T_p=$.

$$\frac{\left(\frac{P}{n}\right)_a - \left(\frac{P}{n}\right)_{ter}}{\left(\frac{P}{n}\right)_a - \left(\frac{P}{n}\right)_b}$$

Where:

P=photon counts at day 'a', day 'ter', or day 'b' where 'a' is the day when drug treatment was stopped and 'ter' is the day when the experiment was terminated and 'b' is the day where P is minimum after day a but before day 'ter'.

n=number of animals alive when P was measured.

The larger the value indicates greater effectiveness of the drug after stopping drug treatment, i.e. the penetrance of the drug over time.

Results

To determine the temporal penetrance of AN019, AN024 and Imatinib, nude mice were implanted with K562luc cells. The animals were imaged at 6 day intervals post transplantation. Drug treatment (AN019 20 mg/kg, AN024 20 mg/kg and Imatinib 10 mg/kg) was initiated 15 days post implantation by daily ip injections. Drug treatment was stopped on day 35 and animals were imaged till day 45, and calculated as described in methods.

By applying the equation for temporal penetrance, $T_p$ values were determined as:

AN019=2.0
AN024=2.4
Imatinib=0.8

These values of $T_p$ indicate that AN024 had activity over untreated controls and fared better than AN019 for activity over time after withdrawal of drug treatment.

Example 6

Figure 4A:
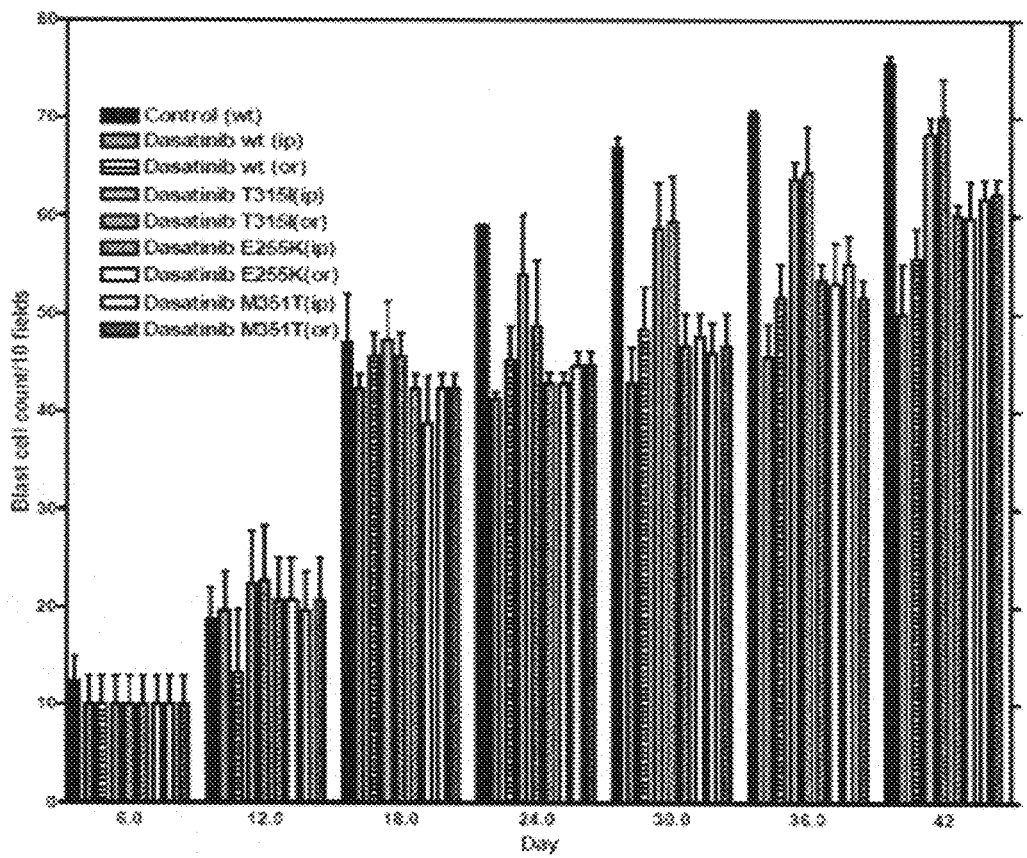
FIGS. 4A, 4B, and 4C. These figures illustrate the results of studies analogous to those illustrated in FIGS. 3A and 3B but employing the control drug Dasatinib.
Figure 4B:
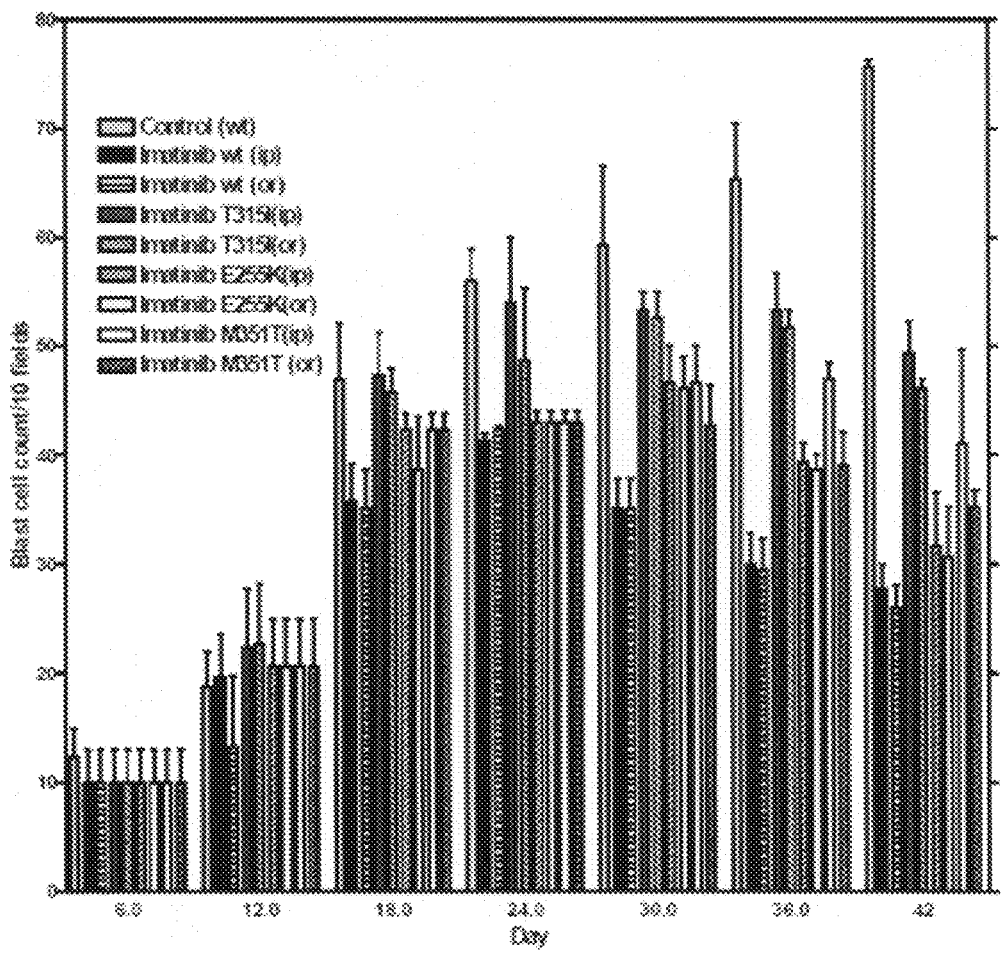
Figure 4C:
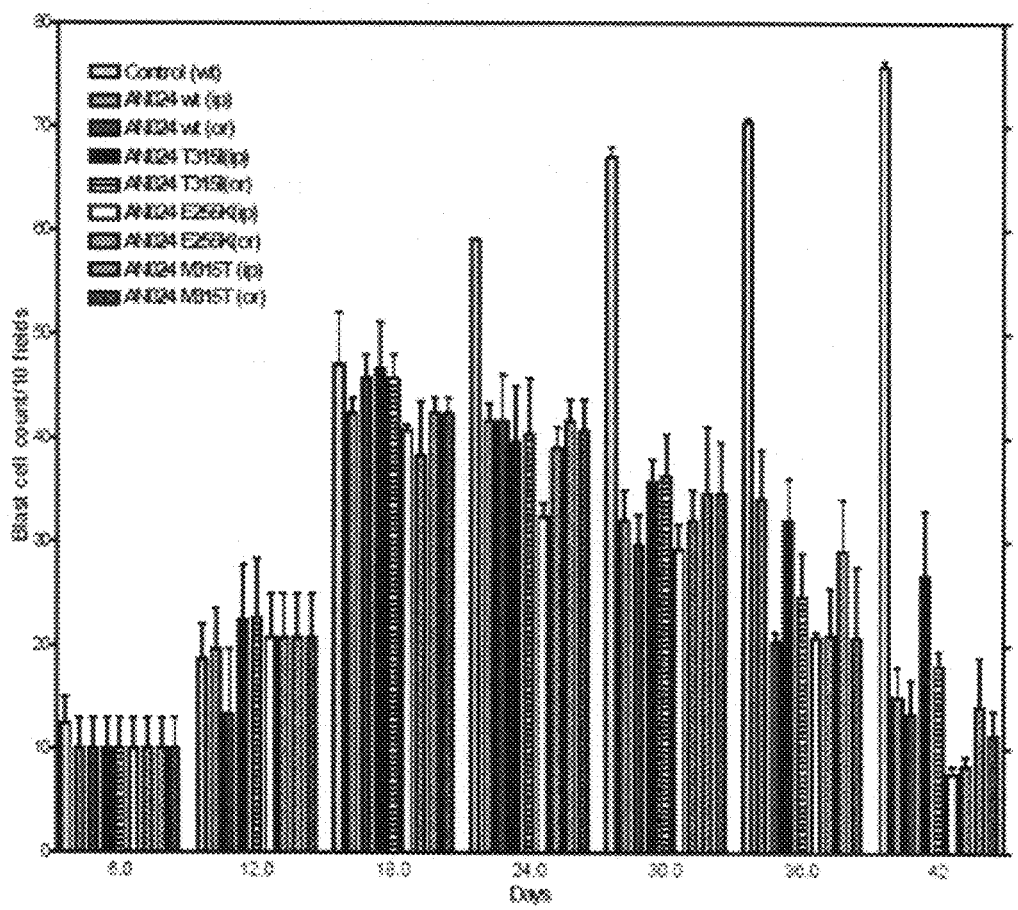

Effect of Dasatinib on Baf3 Implanted Nude Mice When Compared to AN024, AN019 and Imatinib (FIGS. 4A, 4B, and 4C)

Example 3 demonstrated the effectiveness of AN024 and AN019 in the treatment of leukemia when compared to Imatinib by using Baf3 (wt, T315I, M351T and E255K) mutant cell lines. Here, we have used Dasatinib as a control drug to determine the response of Baf3 mutant cells to treatment when compared to AN024 and Imatinib.

Method

The experimental layout is given in the tabular form as follows:

| Controls (previously done) | Treatment | cell line implanted | | | |
|---|---|---|---|---|---|
| | | Wt | T315I | M351T | E255K |
| Dasatinib (10 mg/kg) | oral | 5 | 5 | 5 | 5 |
| | ip | 5 | 5 | 5 | 5 |

Nude mice were intraperitoneally implanted with Baf3 mutant cells (wt, T315I, M351T or E255K). 15 days following implantation, the mice were treated either orally or intraperitoneally with 10 mg/kg Dasatinib for 27 days. Blood was drawn from the femoral vein or tail vein every 6th day and blast cell count determined and graphically represented.

Results

On the $6^{th}$ day, blood smears of nude mice implanted with Baf3 mutant cells (wt, T315I, M351T or E255K) showed normal blast cell count, and blast cell count progressively increased as observed on day 12. Dasatinib treatment was started on day 15 post implantation. Dasatinib treatments fared no better than Imatinib. On day 42, the termination of the experiment, mice implanted with wt cells showed significant response to Dasatinib, indicating that ip treatments were superior to oral. Mice implanted with T315I and M351T cells behaved similar to controls with no significant decrease in blast cell count. Mice implanted with E255K fared only a little better than T315I implanted cells in response to Dasatinib treatment. Overall Dastinib treatment only caused retardation in leukemic progress with no significant curative effect. Blast cell count was much lower in the group treated with AN-024 indicating the superiority and the potential of this compound in treating leukemia better than Imatinib and Dasatinib. These results are illustrated in FIGS. 4A, 4B, and 4C.

Example 7

In Vitro Studies on Glioma and Breast Cell Lines (FIGS. 5A-5D)

Material and Methods

To determine the effect of AN019, AN024 and Temozolomide (TMZ) with or without radiation on glioma and breast cancer cells, cells were treated at the specified doses and determined invasion, angiogenesis and changes in certain signaling molecules.

Matrigel Invasion Assay

The in vitro invasiveness of 4910, 5310 and U87 glioma cells and MDAMB231 and ZR71 breast cancer cells in the presence of specified concentrations of compounds were assessed using a modified Boyden chamber assay. Cells were treated with these compounds for 48 h. $1 \times 10^6$ cells were suspended in 600 µl of serum-free medium supplemented with 0.2% BSA and placed in the upper compartment of the transwell chambers (Corning Costar Fischer Scientific Cat #07-200-158, Pittsburgh Pa.) coated with Matrigel (0.7 mg/ml). The lower compartment of the chamber was filled with 200 µl of serum-medium and the cells were allowed to migrate for 24 h. After incubation, the cells were fixed and stained with Hema-3 and quantified as previously described (Mohanam et al. 1993). The migrated cells were imaged microscopically to determine the reduction in invasiveness induced by the compounds of this invention.

Angiogenic Assay

The in vitro angiogenesis of 4910, 5310 and U87 glioma cells and MDAMB231 and ZR71 breast cancer cells in the presence of specified concentrations of compounds were determined as follows, cells (2×104/well) were seeded in 8-well chamber slides and were treated with various concentrations of test compounds. After a 24 h incubation period, the conditioned media was removed and added to a 4×104 human dermal endothelial cell (monolayer in 8-well chamber slides) and the human dermal endothelial cells were allowed to grow for 72 h. Cells were then fixed in 3.7% formaldehyde and stained with H&E and photographed.

Western Blot Analysis

Western blot analysis of 4910, 5310 and U87 glioma cells and MDAMB231 and ZR71 breast cancer cells in the presence of specified concentrations of compounds were assessed as per standard protocols. Cells were treated with AN019, AN024 or Temozolomide at the specified concentrations. 24 h after treatment, cells were collected and cell lysates extracted. Equal quantities of proteins were fractionated by SDS-PAGE. The fractionated proteins were blotted on to nylon membranes and immunoprobed for AKT, ERK and Pi3k. Breast cancer cell protein isolates were additionally immunoprobed for EGFR, ErbB1, ErbB2 and ErbB3.

Results

Matrigel Invasion Assay

The in vitro invasiveness of 4910, 5310 and U87 glioma cells and MDAMB231 and ZR71 breast cancer cells in the presence of specified concentrations of compounds were assessed using a modified Boyden chamber assay. Cells were treated with these compounds for 48 h. Table 2 shows the results from the studies of in vitro matrigel invasion assay of 4910, 5310 and U87 glioma cells and MDAMB231 and ZR71 breast cancer cells in the presence of specified concentrations of compounds, with and without radiation.

Change in the invasiveness of various cell lines is given in Table 2. From the invasion assay it is evident that AN019 and AN024 were the most effective at inhibiting invasion in a majority of the cells, both with and without radiation.

TABLE 2

| Cell line | Drug | −Radiation % Invasion | +Radiation % Invasion | ±Change in invasion after radiation |
|---|---|---|---|---|
| ZR-71 | Temozolomide | 70% | 65% | −5% |
|  | AN024 | 48% | 45% | −3% |
|  | AN019 | 33% | 19% | −14% |
| MDA-MB-231 | Temozolomide | 62% | 49% | −13% |
|  | AN024 | 43% | 47% | +4% |
|  | AN019 | 45% | 15% | −30% |
| 4910 | Temozolomide | 95% | 73% | −22% |
|  | AN024 | 56% | 39% | −17% |
|  | AN019 | 42% | 15% | −27% |
| 5310 | Temozolomide | 50% | 63% | +13% |
|  | AN024 | 27% | 32% | +5% |
|  | AN019 | 5% | 6% | +1% |
| U87 | Temozolomide | 90% | 93% | +3% |
|  | AN024 | 53% | 29% | −24% |
|  | AN019 | 18% | 18% | 0% |

Figure 5A:
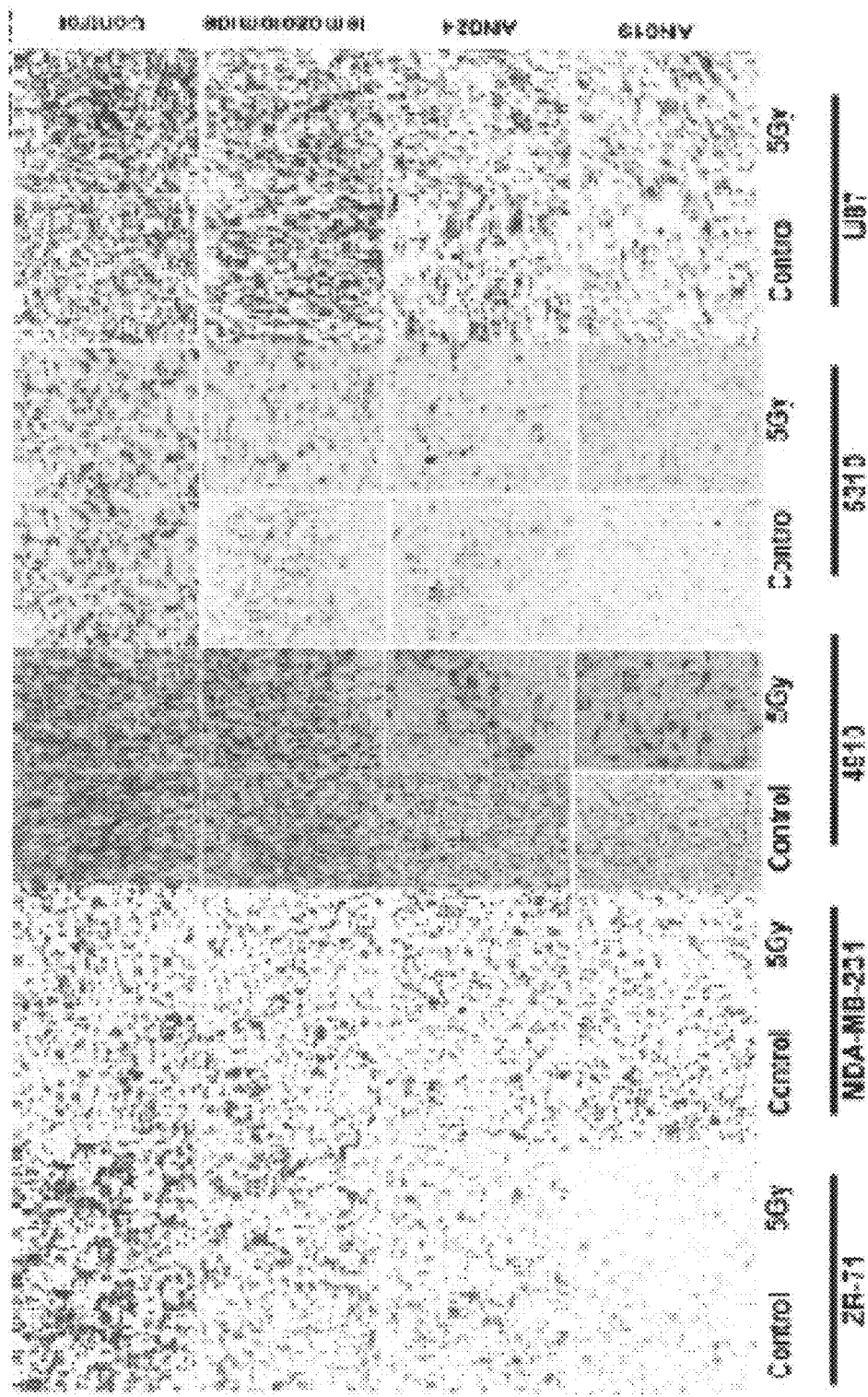
FIGS. 5A and 5B. In vitro matrigel invasion assay of 4910, 5310 and U87 glioma cells and MDAMB231 and ZR71 breast cancer cells in the presence of specified concentrations of AN-024, with and without radiation (Example 7).

FIG. 5A illustrates the results of the in vitro matrigel invasion assay of 4910, 5310 and U87 glioma cells and MDAMB231 and ZR71 breast cancer cells in the presence of specified concentrations of AN-024, with and without radiation.

Figure 5B:
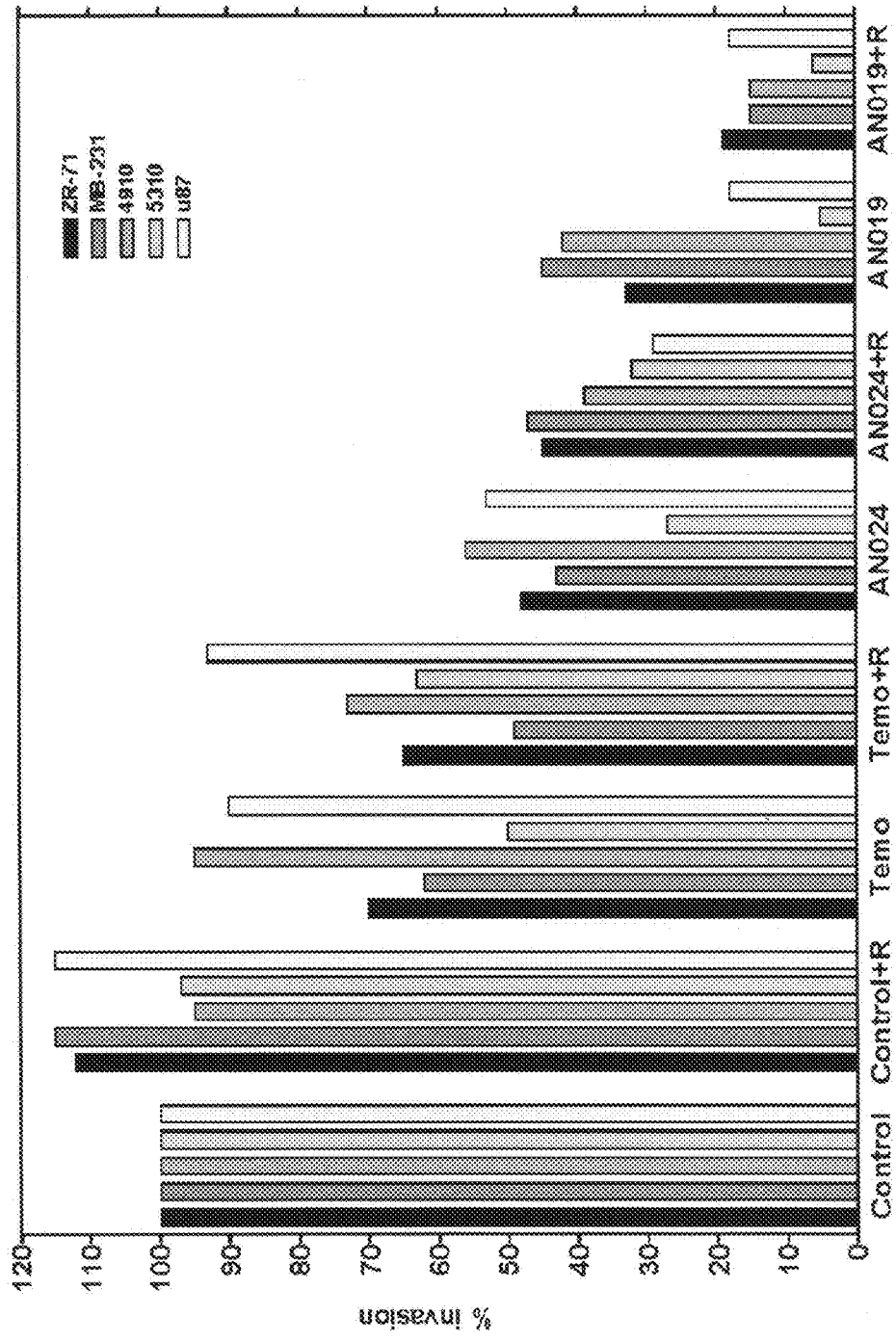

FIG. 5B illustrates the results of the in vitro matrigel invasion assay of 4910, 5310 and U87 glioma cells and MDAMB231 and ZR71 breast cancer cells in the presence of specified concentrations of AN-024, with and without radiation.

Angiogenic Assay

From the angiogenesis assay experiments it is observed that AN019 and AN024 were the most effective at inhibiting angiogenesis.

Temozolomide treatment caused complete inhibition of angiogenesis in ZR-71 cells, whereas in MDA-MB-231 cells only a slight inhibition was observed in control condition with an increase in inhibition after radiation. Glioma xenograft cells 4910 showed significant inhibition of angiogenesis both with and without radiation. In the case of 5310 cells inhibition of angiogenesis was seen in control conditions, whereas angiogenesis was promoted after radiation treatment. U87 glioma cells showed similar inhibition patterns both with and without radiation.

AN024 treatment caused complete inhibition of angiogenesis in ZR-71 cells, whereas in MDA-MB-231 cells only a slight inhibition was observed in control and radiation treatments. Glioma xenograft cells 4910 showed significant inhibition of angiogenesis both with and without radiation. In the case of 5310 cells inhibition of angiogenesis was seen in control conditions, whereas angiogenesis further inhibited after radiation treatment. U87 glioma cells showed significant retardation in angiogenesis with an increase in inhibition after radiation.

AN019 treatment caused complete inhibition of angiogenesis in ZR-71 cells, whereas in MDA-MB-231 cells a slight inhibition was observed in both control and radiation treatments. Glioma xenograft cells 4910 showed inhibition of angiogenesis similar to MDA-MB-231 cells with an increase in angiogenic inhibition after radiation. In the case of 5310 cells inhibition of angiogenesis was greater in control conditions than after radiation treatment. U87 glioma cells showed similar significant retardation in angiogenesis both with and without radiation.

Figure 5C:
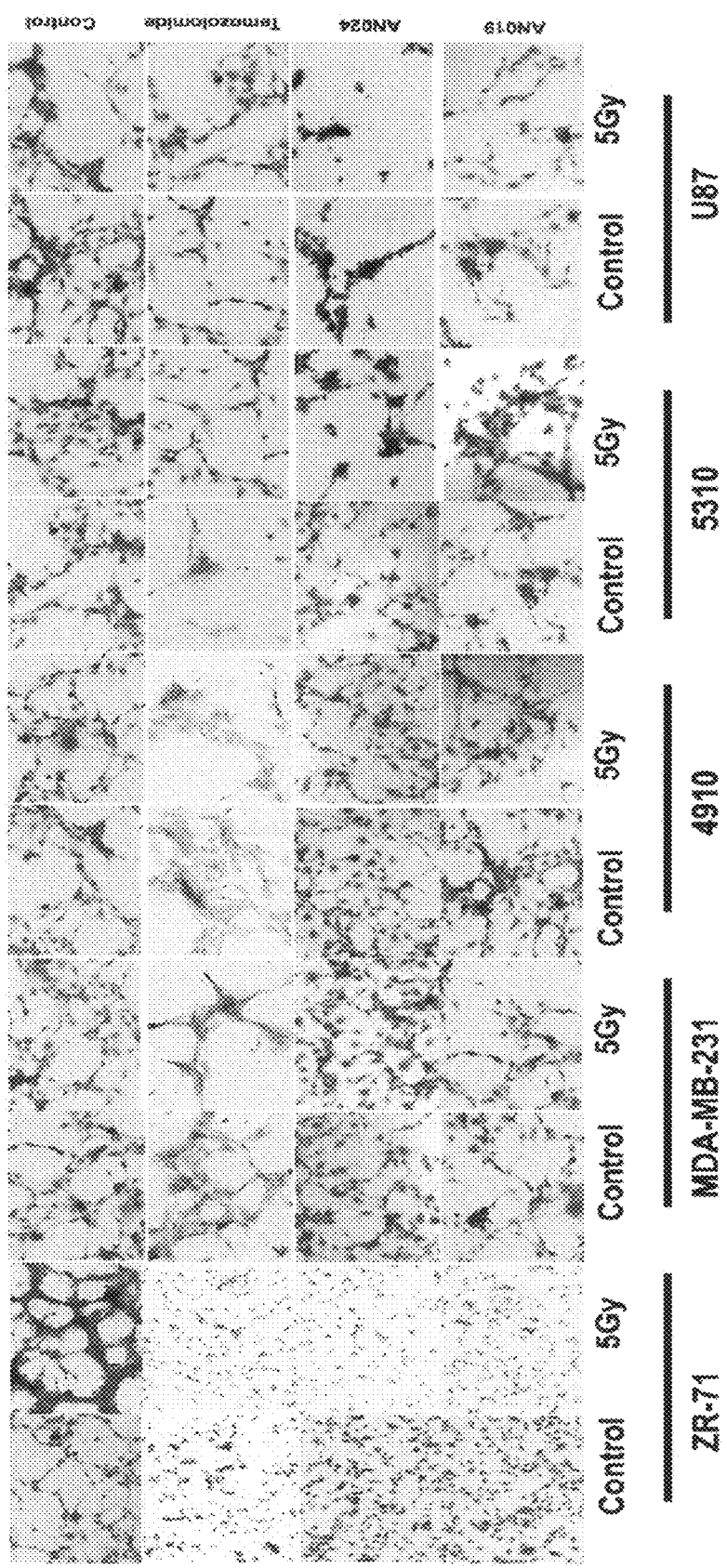
FIG. 5C. In vitro angiogenic assay of 4910, 5310 and U87 glioma cells and MDAMB231 and ZR71 breast cancer cells in the presence of specified concentrations of AN-024, with and without radiation (Example 7).

FIG. 5C illustrates results obtained from the in vitro angiogenic assay of 4910, 5310 and U87 glioma cells and MDAMB231 and ZR71 breast cancer cells in the presence of specified concentrations of AN-024, with and without radiation.

Western Blot Analysis

Western blot analysis of 4910, 5310 and U87 glioma cells and MDAMB231 and ZR71 breast cancer cells in the presence of specified concentrations of compounds of this invention revealed that U87 cells did not show significant change in AKT or PI3k levels both with and without radiation, whereas a slight decrease in ERK levels was observed in AN024 treated cells and decrease was enhanced after radiation. 4910 cells behaved similar to U87 cells with a decrease in AKT levels in after AN024 treatment and the decrease in AKT levels was enhanced after radiation. In case of 5310 cells no significant observable difference was seen in ERK expression whereas AN019 treatment caused a decrease in AKT expression levels. Levels of PI3k were almost undetectable in AN019 treated cells without radiation but reappeared after radiation treatment. In case of breast cancer cells MDA-MB-231 no significant change in AKT, ERK or PI3k was observed, whereas in case of ZR71 AN019 treatment caused a decrease in AKT levels, which was enhanced after radiation. AN024 treatment did not show any significant change under unirradiated conditions, whereas after radiation AN024 treated cells showed a decrease in AKT expression. PI3k levels were absent in AN019 treatments both with and without radiation. AN024 treatment caused decrease in PI3k levels after radiation. Levels of pAKT did not change significantly in any of the treatments with or without radiation, whereas levels of pERK reduced significantly especially in cell treated with AN019 both with and without radiation, AN024 also showed reduction on pERK levels but to a lesser extent than AN019. Temozolomide treatments both with and without radiation did not show any significant change in pAKT of perk levels.

Figure 5D:
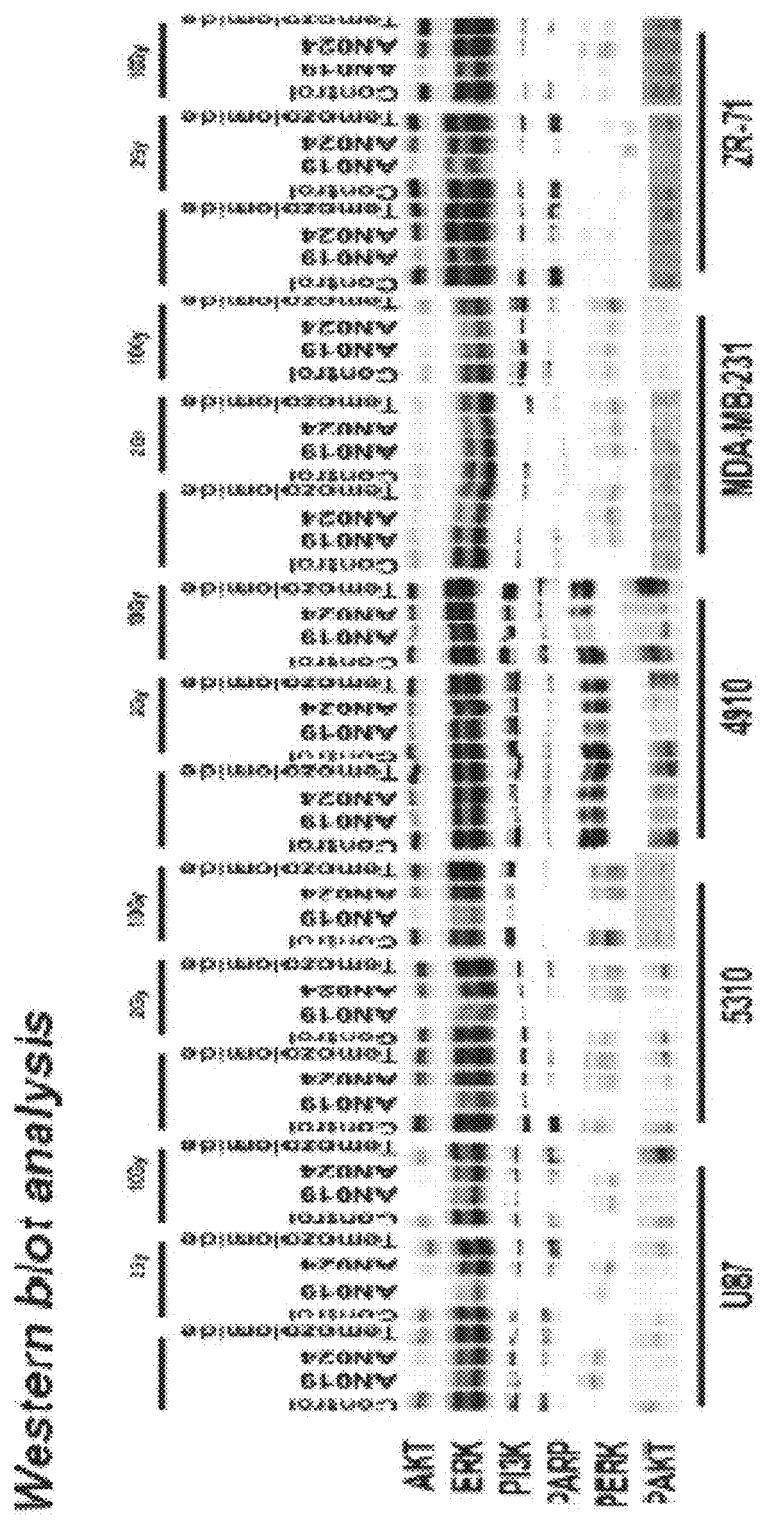
FIG. 5D. Western blot analysis of 4910, 5310 and U87 glioma cells and MDAMB231 and ZR71 breast cancer cells in the presence of specified concentrations of AN-024, with and without radiation (Example 7).

FIG. 5D illustrates the results of Western blot analysis of 4910, 5310 and U87 glioma cells and MDAMB231 and ZR71 breast cancer cells in the presence of specified concentrations of AN-024, with and without radiation.

Example 8

Figure 6A:
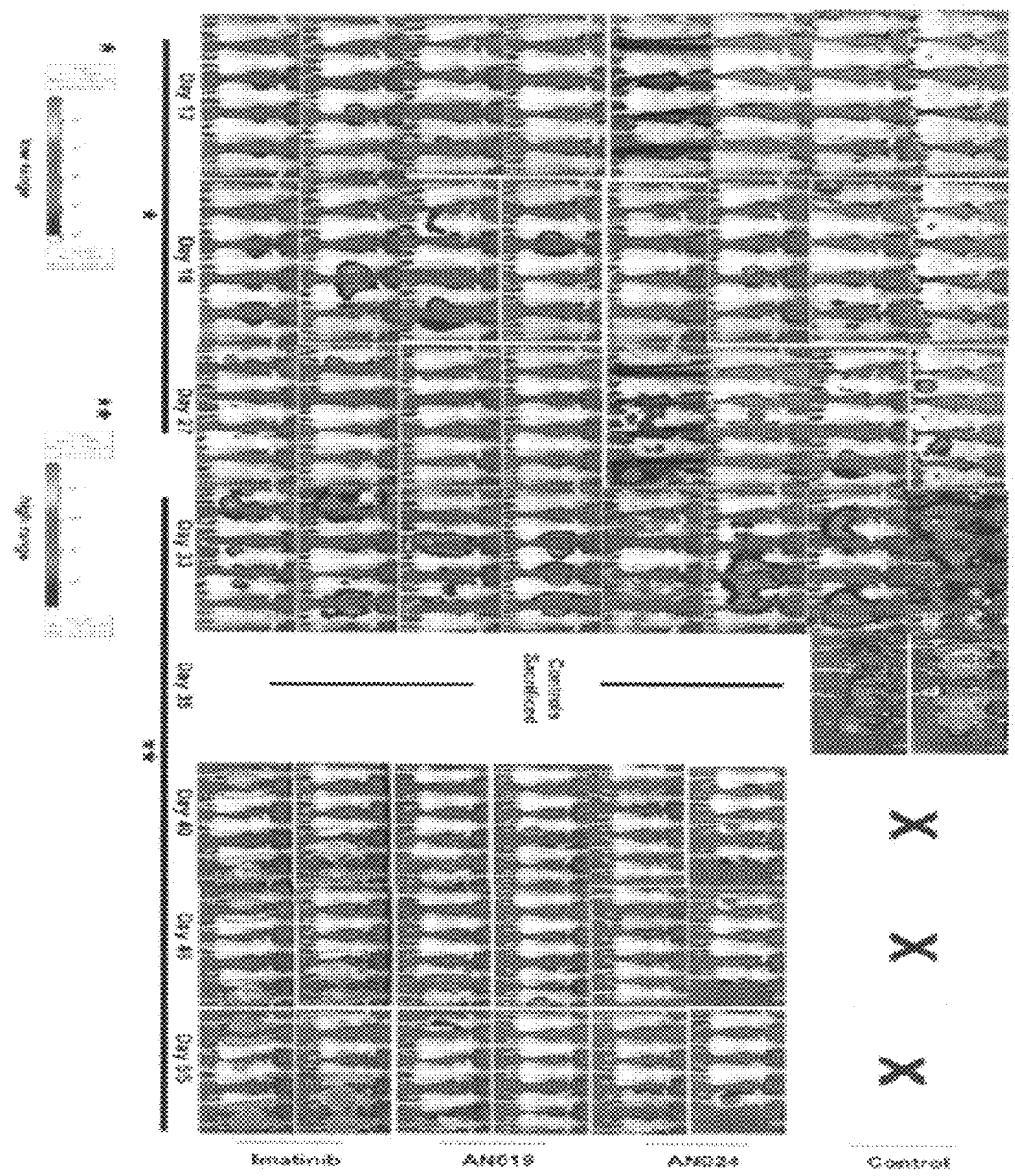
FIG. 6A. Luciferase expression of K562luc implanted mice after treatment with AN024, AN019 or imatinib.
Figure 6B:
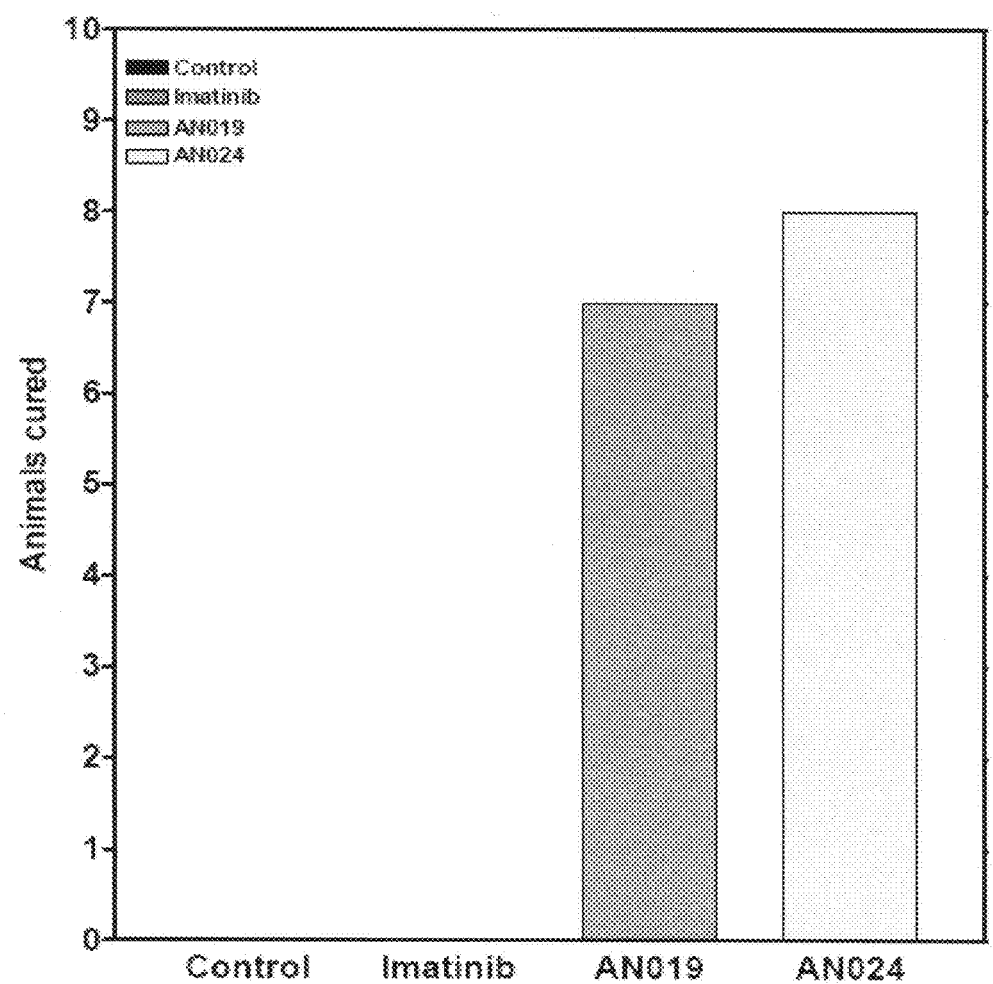
FIG. 6B. Number of animals cured after treatment with AN024 or AN019 at day 58. Drug treatment was stopped at day 42, animals continued to show curative effect after treatment with AN024 and AN019 after withdrawal of drug treatment (Example 8).
Figure 6C:
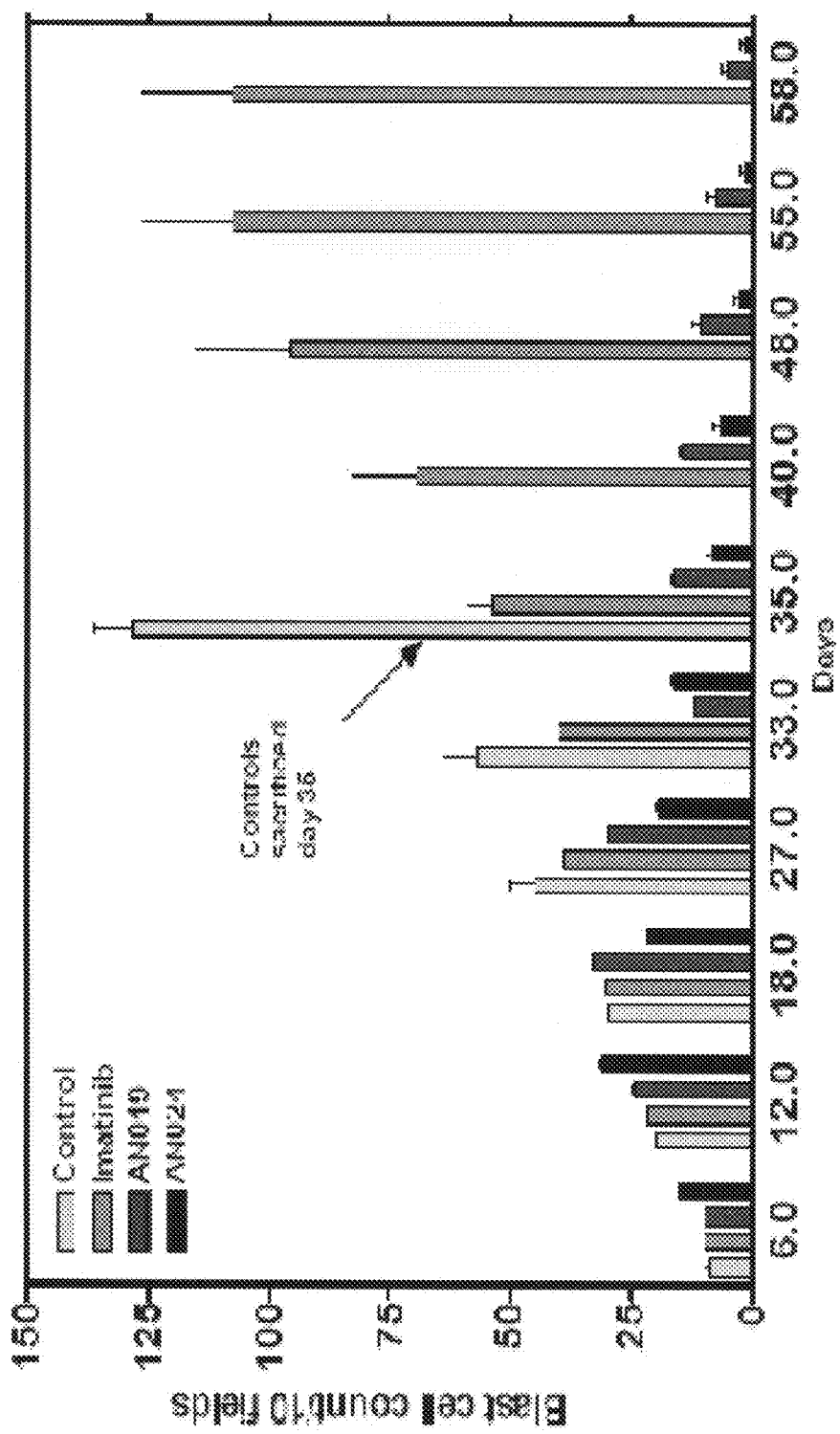
FIG. 6C. Blast cell count from blood smears taken from animals at the day indicated. Drug treatment was withdrawn on day 42. AN024 and AN019 showed effectiveness after withdrawal of drug treatment. Imatinib was found to be ineffective (Example 8).

Leukemic Survival Study (FIGS. 6A-6C)

K562 luciferase expressing cells were implanted intraperitoneally into nude mice; the mice were scanned using the xenogeny IVIS image station after ip injections of luciferin does determine implantations. Drug treatment was started as in previous studies day 15 after implantation. The animals were given treatment till day 42, after which drug treatment was stopped and survival of the animals determined as per the animal care regulations. It was observed that control animals developed leukemia and mortality had occurred on day 34 and 35, as per regulations we were advised to sacrifice the remaining 8 animals on day 35. Drug treatment was withdrawn on day 42 post implantation and survival of animals determined.

Animals treated with AN024 showed mortality on day 38, the dead animals on further inspection did not reveal spleenic enlargement and cause of death was determined to be other than leukemia, blood smears could not be taken from the dead animal. Of the 10 animals used 8 animals showed no signed of leukemia on day 55.

Animals treated with AN019 did not show any mortality and 7 of the 10 animals showed complete absence of leukemic symptoms.

Animals treated with Imatinib showed reoccurrences of leukemic symptoms after treatment withdrawal and showed mortality on day 55, 56, 57 and 58. The surviving animals did show presence of leukemic symptoms.

FIG. 6A illustrates the amount of luciferase expression of K562luc obtained from implanted mice after treatment with AN024, AN019 or imatinib.

FIG. 6B illustrates the number of animals cured after treatment with AN024 or AN019 at day 58. Drug treatment was stopped at day 42, animals continued to show curative effect after treatment with AN024 and AN019 after withdrawal of drug treatment.

FIG. 6C illustrates blast cell count from blood smears taken from animals at the day indicated. Drug treatment was withdrawn on day 42. AN024 and AN019 showed effectiveness after withdrawal of drug treatment.

Example 8A

Studies on $ED_{50}$, $LD_{50}$, MTD and Therapeutic Index

The following table summarizes $ED_{50}$, $LD_{50}$, early cited MTD (Maximum Tolerated Dose) and therapeutic index of the compounds of the present invention in comparison with Imatinib. Methods employed as per J. Pharmacol. Exp. Ther., (1949), 96: 96-113.

| Experimental substance | $LD_{50}$ (po) Mice (mg/Kg) | $ED_{50}$ (po) Mice (mg/Kg) | MTD Mice (mg/Kg) | Therapeutic* index - $LD_{50}/ED_{50}$ |
|---|---|---|---|---|
| Imatinib mesylate | 949 | 12 | 250 | 78.9 |
| AN-019 | 1133 | 11.5 | 500 | 98.5 |
| AN-024 | 1440 | 10 | 500 | 144 |

*Leukemic mice (K562)

Example 9

Figure 7A:
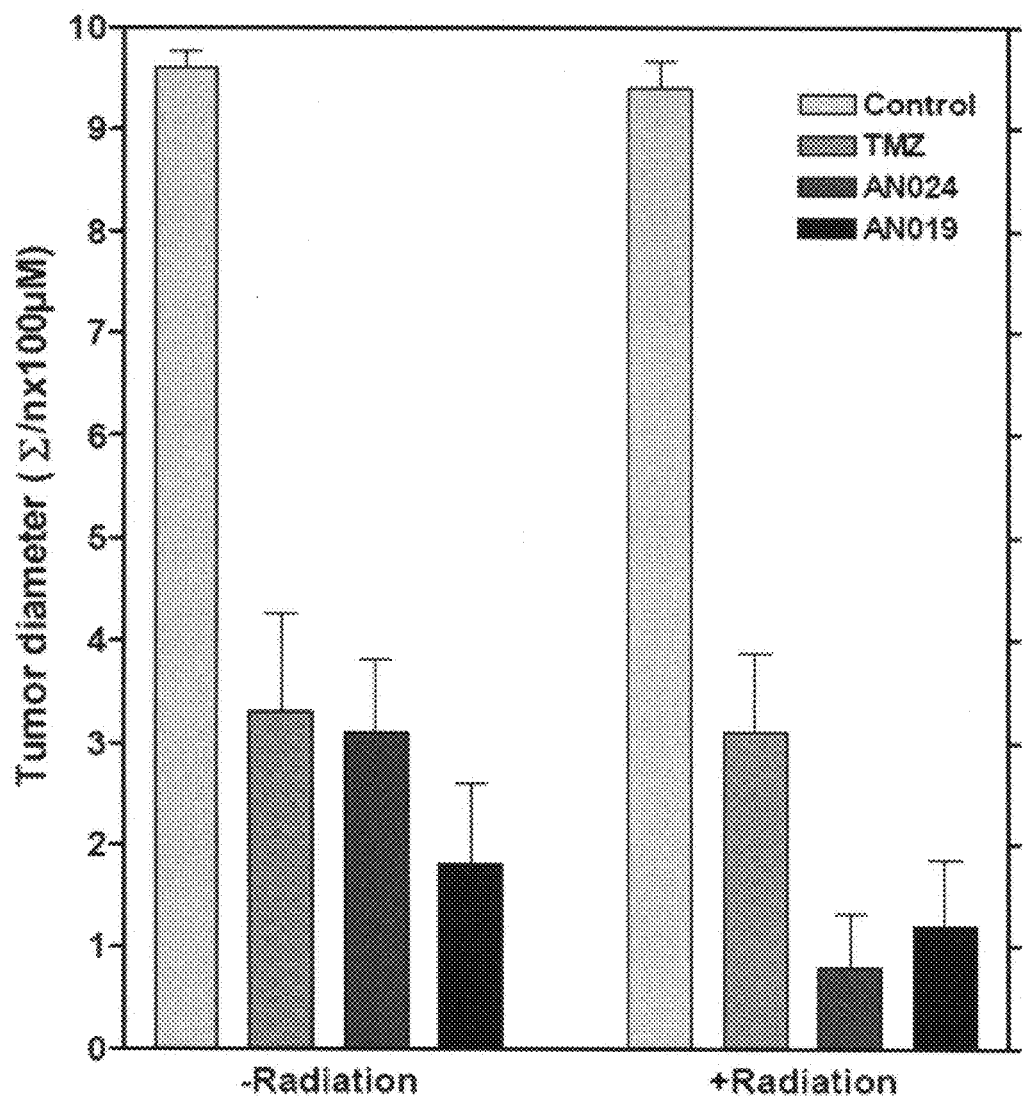
FIG. 7A. Semiquantitative analysis of intracranial tumours in nude mice after treatment with TMZ, AN024 or AN019 with or without radiation (5 Gy) (Example 9).
Figure 7B:
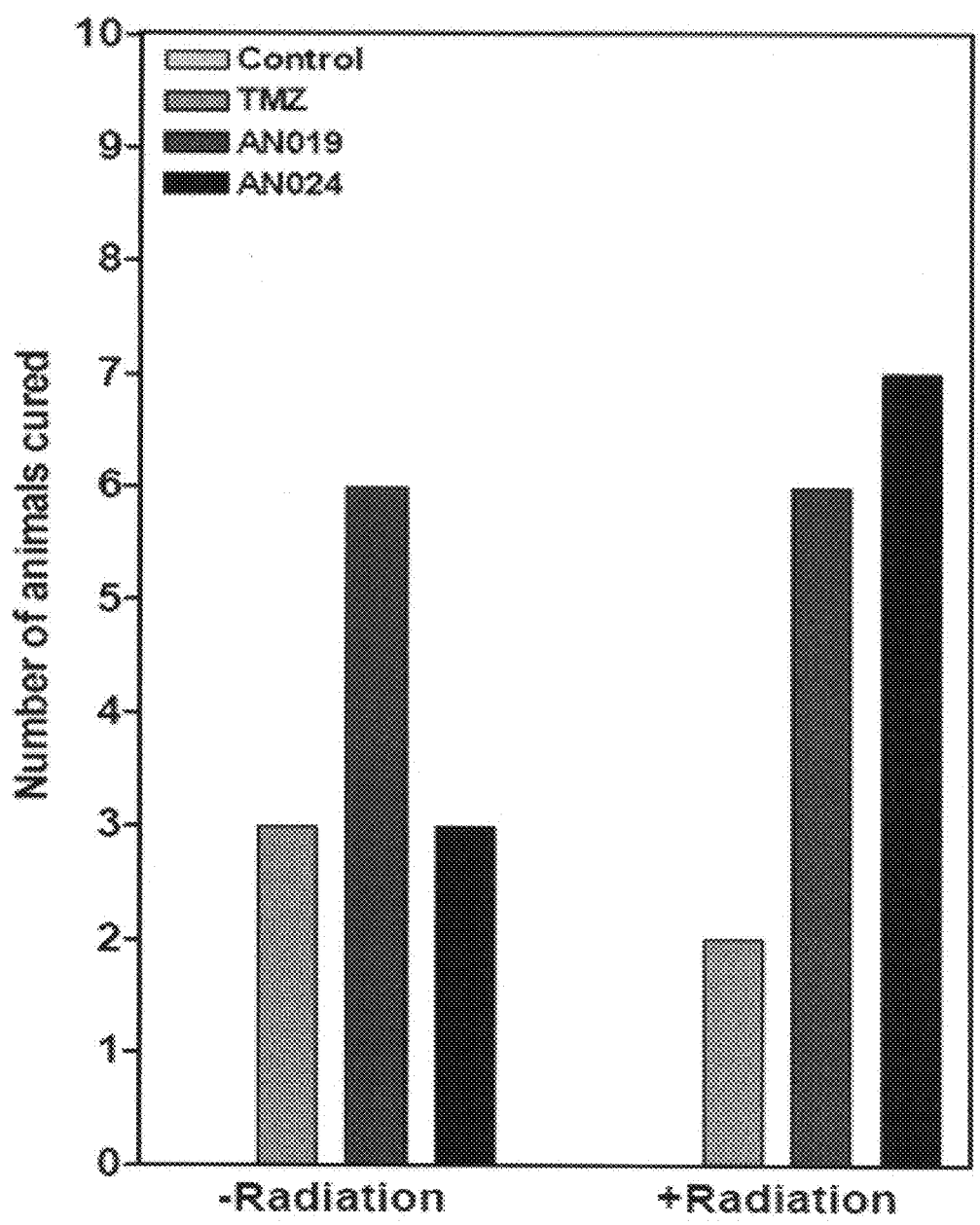
FIG. 7B. Graphical representations of nude mice showing absence of intracranial tumours after drug treatment with AN-024 and without radiation treatments (Example 9).

Glioma Radiation Studies (FIGS. 7A and 7B)

Nude mice were intracranially implanted with 4910 human glioma xenograft cells ($1 \times 10^6$ cells) intracranially. Ten days after implantation mice were treated with AN019, AN024 or temozolomide with or without radiation (5 Gy/week). The experiment was terminated at day 40 post implantation.

From the results it was observed that 100% of control animals developed intracranial tumours and radiation alone had very little effect on tumor size reduction. Animals treated with TMZ alone showed reduction in intracranial tumours with 3 of 10 animals showing complete absence of tumours. Radiation treatment combined with TMZ administration caused a further regression in tumor size with animals showing less symptoms of intracranial pressure (arched back), in this case 2 of the 10 animals showed no observable intracranial tumor.

Animals treated with AN024 without radiation showed presence of intracranial tumours but the tumours were well defined and not showing diffuse edges as seen in controls or TMZ treatments, 3 of 10 animals were cured. After radiation treatment 7 of 10 animals were cured, the animals that showed presence of tumours showed well defined surgically respectable tumours.

Animals treated with AN019 alone showed tumours similar to AN024 treated animals and in this case both with and without radiation 6 of 10 animals were cured. It was observed that after radiation the tumor size was significantly reduced.

FIG. 7A illustrates results obtained from semiquantitative analysis of intracranial tumours in nude mice after treatment with TMZ, AN024 or AN019 with or without radiation (5 Gly).

FIG. 7B shows graphical representations of nude mice showing absence of intracranial tumours after drug treatment with AN-024 and without radiation treatments.

The preparative synthetic and other aspects of the compounds of the present invention have been illustrated in the following examples.

Example 10

(a) Preparation of (3-trifluoromethylsulfonyl)-N-[4-methyl-3-nitrophenyl]-benzamide (formula (III))

A solution of 336 gms (6 moles) of potassium hydroxide in 1040 ml of water was slowly added to a suspension of 22.8 gins (0.15 moles) of 4-methyl-2-nitro aniline of formula (II) and 163.5 gms (0.6 moles) of (3-trifluomethylsulfonyl) benzoyl chloride of formula (VI) in 380 ml chloroform at 30 to 40° C. for 3 to 4 hours. Then the chloroform layer was separated and washed with water. The organic layer was dried over anhydrous sodium sulfate and solvent was removed under vacuum to obtain compound of formula (III) 180 ml isopropylether was added to the residue and filtered Yield: 42 gms (90.6%)
Purity: 98.5% (by HPLC)
IR and NMR were consistent with the proposed structure.

(b) Preparation of the (3-trifluoromethylsulfonyl)-N-[3-amino-4-methylphenyl]-benzamide (formula (IV))

A suspension of 42.6 gms (0.11 moles) of (3-trifluoromethylsulfonyl)-N-[4-methyl-3-nitrophenyl]-benzamide of formula (III) obtained from step (a) in 100 ml conc. hydrochloric acid slowly to solution of 145.9 gms (0.65 moles) stannous chloride in 390 ml conc. hydrochloric acid at 0 to 5° C. for a period of 30 minutes. The reaction mass was brought to room temperature and maintained for 2 hours. Aqueous 50% sodium hydroxide solution was slowly added to the reaction mass to 30 to 40° C. extracted the product into chloroform (2×500 ml) washed with water (2×500 ml). The chloroform layer was given activated carbon (4 gms) treatment, filtered and dried over anhydrous sodium sulfate. The solvent was removed by distillation and the residue was dissolved in 250 ml acetone treated with isopropylalcoholic hydrochloride and stirred at room temperature for 3 to 4 hours. The hydrochloride salt of formula (IV) was filtered and washed with acetone dried at 50-60° C. under vacuum Yield: 25 gms (61%)
IR and NMR were consistent with the proposed structure.

(c) Preparation of (3-trifluoromethylsulfonyl)-N-[3-guanidino-4-methylphenyl]-benzamide HCl (formula (V))

A solution of 2.2 gms (0.52 moles) of cyanamide in 2 ml water was added to a suspension of 10.25 gms (0.026 moles) of (3-trifluoromethylsulfonyl)-N-[3-amino-4-methylphenyl]-benzamide of formula (IV) obtained from step b in 65 ml n-butanol at 90° C. for 10 minutes. The reaction was maintained at 90-92° C. for 1 hour and filtered. It was dried at 60-70° C. under vacuum.

Yield: 6.1 gms (61%)
IR and NMR were consistent with the proposed structure.

(d) Preparation of (3-trifluoromethylsulfonyl)-N-[4-methyl-3-(4-pyridin-3yl-pyrimidin-2ylamino)-phenyl]-benzamide (formula (I))

A mixture of 7.8 gms (0.018 moles) of (3-trifluoromethylsulfonyl)-N-[3-guanidino-4-methylphenyl]-benzamide hydrochloride of formula (V) from step (c) 3.1 gms (0.018 moles) of 3-dimethylamino-1-pyridin-3-yl-propenone (formula VII) and 0.7 gms (0.018 moles) of sodium hydroxide flakes in 60 ml n-butanol was heated at 110° C. for 7 hours. The solvent was removed by distillation and the residue was treated with 75 ml water and filtered. The filtered compound was dissolve in 75 ml chloroform and carbon treatment was given. Chloroform layer was washed with 5% sodium hydro sulfite solution (50 ml) and then with water. The solvent was removed by distillation and the compound of formula (I) was precipitated by adding a mixture of 10 ml chloroform and 50 ml ethyl acetate to the residue. The solid was filtered and washed with ethyl acetate dried at 50-60° C. under vacuum Yield: 5 gms (56%)
MR: 214-218° C.
IR and NMR were consistent with the proposed structure.

Advantages of embodiments of the present invention can include:
1. Intermediates of formulae (III), (IV), and (V).
2. The compound of formula I was found to be a useful anti tumor agent as evidenced by all the biological tests.

As used herein, the term "about" refers to the variation in an amount or range that is conventional for the field of organic chemistry, for example, the typical variation that occurs in temperatures or times as measured in real world situations in the organic chemistry laboratory, scale-up, or production facility, or in evaluating anti-proliferative agents. Any range or amount used in the description of the present invention that is modified by the term "about" is also a part of the invention if not modified by the term about. For example, recitation of "about 10 to about 20" also includes recitation of "10 to 20".

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:
1. A compound of formula I:

2. A method of treating a leukemia, a glioma, or a breast cancer, comprising administering to a subject in need of treatment for a leukemia, a glioma, or a breast cancer, a compound of formula:

3. A compound (3-trifluoromethylsulfonyl)-N-[4-methyl-3-nitrophenyl]-benzamide.

4. A method of preparing (3-trifluoromethylsulfonyl)-N-[4-methyl-3-nitrophenyl]-benzamide, the method comprising:
   providing (3 trifluomethylsulfonyl)benzoyl chloride;
   condensing 4-methyl-2-nitro-aniline with the compound of formula (VI)

$$\text{(VI)}$$

[structure: benzene ring with COCl and SO$_2$CF$_3$ substituents]

at about 30 to about 40° C. in chlorohydrocarbon solvent with aqueous alkali addition to obtain (3-trifluoromethylsulfonyl)-N-[4-methyl-3-nitrophenyl]-benzamide.

5. A compound (3-trifluoromethylsulfonyl)-N-[3-amino-4-methylphenyl]-benzamide.

6. A method of preparing (3-trifluoromethylsulfonyl)-N-[3-amino-4-methylphenyl]-benzamide, the method comprising:
   providing (3-trifluomethylsulfonyl)benzoyl chloride;
   condensing 4-methyl-2-nitro-aniline with the compound of formula (VI)

$$\text{(VI)}$$

[structure: benzene ring with COCl and SO$_2$CF$_3$ substituents]

at about 30 to about 40° C. in chlorohydrocarbon solvent with aqueous alkali addition to obtain (3-trifluoromethylsulfonyl)-N-[4-methyl-3-nitrophenyl]-benzamide;
   reducing the (3-trifluoromethylsulfonyl)-N-[4-methyl-3-nitrophenyl]-benzamide with stannous chloride and concentrated HCl at about 0 to about 5° C. for about 3 to about 4 hours to obtain (3-trifluoromethylsulfonyl)-N-[3-amino-4-methylphenyl]-benzamide.

7. A compound (3-trifluoromethylsulfonyl)-N-[3-guanidino-4-methylphenyl]-benzamide.

8. A method of preparing (3-trifluoromethylsulfonyl)-N-[3-guanidino-4-methylphenyl]-benzamide, the method comprising:
   providing (3-trifluomethylsulfonyl)benzoyl chloride;
   condensing 4-methyl-2-nitro-aniline with the compound of formula (VI)

$$\text{(VI)}$$

[structure: benzene ring with COCl and SO$_2$CF$_3$ substituents]

at about 30 to about 40° C. in chlorohydrocarbon solvent with aqueous alkali addition to obtain (3-trifluoromethylsulfonyl)-N-[4-methyl-3-nitrophenyl]-benzamide;
   reducing the (3-trifluoromethylsulfonyl)-N-[4-methyl-3-nitrophenyl]-benzamide with stannous chloride and concentrated HCl at about 0 to about 5° C. for about 3 to about 4 hours to obtain (3 trifluoromethylsulfonyl)-N-[3-amino-4-methylphenyl]-benzamide;
   condensing the (3-trifluoromethylsulfonyl)-N-[3-amino-4-methylphenyl]-benzamide with aqueous cyanamide at about 90 to about 95° C. in n-butanol solvent to obtain (3-trifluoromethylsulfonyl)-N-[3-guanidino-4-methylphenyl]-benzamide.

9. A method of preparing compound of formula I:

[structure of formula I: pyrimidine linked via NH to methylphenyl linked via NH-C(=O) to benzene with SO$_2$CF$_3$; pyrimidine bears pyridin-3-yl]

the method comprising:
   providing (3-trifluomethylsulfonyl)benzoyl chloride;
   condensing 4-methyl-2-nitro-aniline with the compound of formula (VI)

$$\text{(VI)}$$

[structure: benzene ring with COCl and SO$_2$CF$_3$ substituents]

at about 30 to about 40° C. in chlorohydrocarbon solvent with aqueous alkali addition to obtain (3-trifluoromethylsulfonyl)-N-[4-methyl-3-nitrophenyl]-benzamide;
   reducing the (3-trifluoromethylsulfonyl)-N-[4-methyl-3-nitrophenyl]-benzamide with stannous chloride and concentrated HCl at about 0 to about 5° C. for about 3 to about 4 hours to obtain (3 trifluoromethylsulfonyl)-N-[3-amino-4-methylphenyl]-benzamide;
   condensing the (3-trifluoromethylsulfonyl)-N-[3-amino-4-methylphenyl]-benzamide with aqueous cyanamide at about 90 to about 95° C. in n-butanol solvent to obtain (3-trifluoromethylsulfonyl)-N-[3-guanidino-4-methylphenyl]-benzamide;
   condensing the (3-trifluoromethylsulfonyl)-N-[3-guanidino-4-methylphenyl]-benzamide with 3-dimethylamino-1-pyridin-3-yl-propenone in presence of base at reflux temperature to obtain the compound of formula (I).

* * * * *

UNITED STATES PATENT AND TRADEMARK OFFICE
CERTIFICATE OF CORRECTION

PATENT NO. : 7,939,541 B2 Page 1 of 1
APPLICATION NO. : 12/042240
DATED : May 10, 2011
INVENTOR(S) : Kompella et al.

It is certified that error appears in the above-identified patent and that said Letters Patent is hereby corrected as shown below:

Col. 17, line 28, claim 6: "4-methyl-2-nitro-aniline" should read --4-methyl-3-nitro-aniline--

Col. 17, line 54, claim 8: "4-methyl-2-nitro-aniline" should read --4-methyl-3-nitro-aniline--

Col. 18, line 32, claim 9: "4-methyl-2-nitro-aniline" should read --4-methyl-3-nitro-aniline--

Signed and Sealed this
Thirty-first Day of July, 2012

David J. Kappos
*Director of the United States Patent and Trademark Office*